(12) United States Patent
Portnoy et al.

(10) Patent No.: US 7,794,728 B2
(45) Date of Patent: Sep. 14, 2010

(54) **ATTENUATED *LISTERIA SPP.* AND METHODS FOR USING THE SAME**

(75) Inventors: Daniel A. Portnoy, Albany, CA (US);
Mary O'Riordan, Alameda, CA (US);
Ian Glomski, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/449,710

(22) Filed: May 29, 2003

(65) Prior Publication Data

US 2004/0013690 A1   Jan. 22, 2004

Related U.S. Application Data

(60) Provisional application No. 60/385,183, filed on May 29, 2002.

(51) Int. Cl.
*C07K 14/195* (2006.01)
(52) U.S. Cl. .................................. 424/200.1; 435/252.1
(58) Field of Classification Search .............. 435/252.3, 435/93.2, 6, 69.1, 243, 320.1, 325; 424/200.1, 424/192.1, 190.1, 193.1; 536/24.32, 23.7, 536/24.3
See application file for complete search history.

(56) References Cited

U.S. PATENT DOCUMENTS

| | | | |
|---|---|---|---|
| 4,816,253 A | | 3/1989 | Likhite |
| 5,389,513 A | | 2/1995 | Baquero et al. |
| 5,643,599 A | * | 7/1997 | Lee et al. ..................... 424/450 |
| 5,830,702 A | * | 11/1998 | Portnoy et al. .............. 435/69.3 |
| 6,004,815 A | * | 12/1999 | Portnoy et al. ............... 435/454 |
| 6,051,237 A | * | 4/2000 | Paterson ................... 424/200.1 |
| 6,099,848 A | * | 8/2000 | Frankel et al. ............ 424/246.1 |
| 6,287,556 B1 | * | 9/2001 | Portnoy et al. .............. 424/93.1 |
| 6,504,020 B1 | * | 1/2003 | Frankel et al. .............. 536/23.1 |

(Continued)

FOREIGN PATENT DOCUMENTS

WO    WO 99/25376    5/1999

(Continued)

OTHER PUBLICATIONS

Ripio, Maria-Teresa, Journal of Bacteriology, Mar. 1997, vol. 179(5), pp. 1533-1540, A Gly145Ser substitution in the trascriptional activator PrfA causes consittutive overexpression of virulence factors in *Listeria monocytogenes*.*

(Continued)

*Primary Examiner*—Robert B Mondesi
*Assistant Examiner*—Ginny Portner
(74) *Attorney, Agent, or Firm*—Bret E. Field; Bozicevic, Field & Francis LLP

(57) ABSTRACT

Attenuated *Listeria* bacteria are provided. The subject bacteria are characterized by having a mutation in a gene chosen from the IplA gene and the hly gene. The subject bacteria find use in a variety of applications, where representative applications of interest include, but are not limited to: (a) use of the subject bacteria as adjuvants; (b) use of the subject bacteria as delivery vectors for introducing macromolecules into a cell; (c) use of the subject bacteria as vaccines for eliciting or boosting a cellular immune response; etc.

36 Claims, 6 Drawing Sheets

U.S. PATENT DOCUMENTS

| | | | |
|---|---|---|---|
| 6,599,502 B2 * | 7/2003 | Portnoy et al. | 424/93.1 |
| 6,767,542 B2 * | 7/2004 | Paterson et al. | 424/192.1 |
| 6,825,028 B1 * | 11/2004 | Von Eichel-Streiber et al. | 435/252.3 |
| 2004/0228877 A1 * | 11/2004 | Dubensky et al. | 424/200.1 |
| 2005/0249748 A1 * | 11/2005 | Dubensky et al. | 424/190.1 |
| 2006/0078901 A1 * | 4/2006 | Buchrieser et al. | 435/6 |
| 2006/0093582 A1 * | 5/2006 | Paterson et al. | 424/93.2 |
| 2006/0104991 A1 * | 5/2006 | Paterson et al. | 424/200.1 |
| 2006/0210540 A1 * | 9/2006 | Paterson et al. | 424/93.2 |
| 2006/0233835 A1 * | 10/2006 | Paterson et al. | 424/234.1 |
| 2007/0059322 A1 * | 3/2007 | Portnoy et al. | 424/200.1 |
| 2007/0253976 A1 * | 11/2007 | Paterson et al. | 424/197.11 |
| 2007/0264279 A1 * | 11/2007 | Gravekamp et al. | 424/190.1 |

FOREIGN PATENT DOCUMENTS

| | | |
|---|---|---|
| WO | WO 00/09733 | 2/2000 |
| WO | 0177335 A2 * | 10/2001 |
| WO | WO 01/77335 | 10/2001 |

OTHER PUBLICATIONS

Ward, TJ et al, Journal of Bacteriology, Aug. 2004, vol. 186(15), pp. 4994-5002.*

Decatur, AL et al, Nov. 3, 2000, Science, vol. 290, pp. 992-995.*

Glomski, Ian J. et al, The Journal of Cell Biology, vol. 156(6), Mary 18, 2002, pp. 1029-1038.*

Leimeister-Wachter, M et al, Infection and Immunity, Aug. 1989, vol. 57(8), pp. 2350-2357.*

Swiss Prot Accession No. Q4EEB1, listeriolysin O.*

Swiss Prot Accession No. Q724L1, lysteriolysin O.*

Swiss Prot Accession No. P13128, Listeriolysin O.*

Swiss Prot Accession No. Q6RD0, gene name hly.*

Swiss Prot Accession No. Q6R6C1, gene name hly.*

Swiss Prot Accession No. Q4EH75, gene name hly-III, protein name hemolysin III of *Listeria monocytogenes*.*

Swiss Prot Accession No. Q71YF2, gene name hly-III, protein name hemolysin III of *Listeria monocytogenes*.*

Dramsi, S et al, The Journal of Cell Biology, vol. 156(6), pp. 943-946, Mar. 18, 2002.*

Darji, A et al, Journal of Biotechnology, vol. 43, pp. 205-212, 1995.*

Rapio, MT et al, Res. Microbiol. 1996, vol. 147, pp. 371-384.*

Cossart, P et al, Infection and Immunity, Nov. 1989, vol. 57(11), p. 3629-3636.*

Lety, Marie-Annick et al, Molecular Immunology, vol. 39(5), pp. 1124-1139, 2001.*

Leece, JG et al, Can. J. Comp. Med. Jan. 1979, vol. 43, pp. 90-93.*

Jacobson, Robert M. et al, Vaccine, vol. 19, pp. 2428-2433, 2001, Adverse events and vaccination- the lack of power and predictability of infrequent envents in pre-licensure study.*

Dazzi, F et al, Clinical Immunology and Immunopathology, vol. 75(1), pp. 26-32, Apr. 1995.*

Bockmann, R et al, Molecular Microbiology, vol. 36(2), pp. 487-497, 2000, PrfA mediates specific binding of RNA polymerase of *Listeria monocytogenes* to FrfA-dependent virulence gene promoters resulting in a transcriptionally active complex.*

Dramsi, Shaynoor et al, The Journal of Cell Biology, vol. 156(6), pp. 943-946, Mar. 18, 2002.*

Decatur, Amy L et al, Science, vol. 290, Nov. 3, 2000, pp. 992-995.*

Glomski, Ian J et al, The Journal of Cell Biology, Mar. 18, 2002, pp. 1029-1038, vol. 156(6).*

Ellis, Ronald W. PhD, chapter 29, New Technologies for Making Vaccines, pp. 568-575, in Vaccines, WB Saunders Co., 1988.*

Boslego, John W. et al, Chapter 17, pp. 211-223, in Vaccines and Immunotherapy, 1991, Pergamon Press, Gonorrhea vaccines.*

Camilli, Andrew et al, PNAS (USA) vol. 86, pp. 5522-5526, Jul. 1989, Intracellular methicillin selection of *Listeria monocytogenes* mutants unable to replicate in a macrophage cell line.*

O'Riordan, Mary et al, Science, vol. 302, pp. 462-464, 2003, *Listeria* intracelluar growth and virulence require host derived lipoic acid.*

Embl Accession No. EU262934, Nov. 19, 2007, *Listeria monocytogenes* lipoate protein ligase gene, genomic DNA sequence.*

Ripio et al. "A Gly145Ser Substitution in the Transcriptional Activator PrfA Causes Constitutive Overexpression of Virulence Factors in *Listeria monocytogenes*" *Journal of Bacteriology*, Mar. 1997, p. 1533-1540.

Darji et al. "Hyperexpression of Listeriolysin in the nonpathogenic species *Listeria innocua* and high yield purification" *Journal of Biotechnology* Dec. 15, 1995, vol. 43, No. 3 pp. 205-221 (abstract only).

Portnoy, Daniel ER AL: "The Cell Biology 1-22 of *Listeria monocytogenes* infection: the cell-mediated immunity." The Journal of Cell Biology, Aug. 5, 2002, vol. 158, No. 33, pp. 409-414.

* cited by examiner

A.

B.

SEQUENCE LISTING

<160> NUMBER OF SEQ ID NOS: 44

<210> SEQ ID NO 1
<211> LENGTH: 34
<212> TYPE: DNA
<213> ORGANISM: L.monocytogenes

<400> SEQUENCE: 1
ggaattccat atgaaggatg catctgcatt caat                                    34

<210> SEQ ID NO 2
<211> LENGTH: 50
<212> TYPE: DNA
<213> ORGANISM: L.monocytogenes

<400> SEQUENCE: 2
cgggatcctt attagtggtg gtggtggtgg tgttcgattg gattatctac                   50

<210> SEQ ID NO 3
<211> LENGTH: 38
<212> TYPE: DNA
<213> ORGANISM: L.monocytogenes

<400> SEQUENCE: 3
ggaattccca tgggaaagga tataacagat aaaaatca                                38

<210> SEQ ID NO 4
<211> LENGTH: 54
<212> TYPE: DNA
<213> ORGANISM: L.monocytogenes

<400> SEQUENCE: 4
cgggatcctt attagtggtg gtggtggtgg tgattgtaag taatactaga tcca              54

<210> SEQ ID NO 5
<211> LENGTH: 29
<212> TYPE: DNA
<213> ORGANISM: L.monocytogenes

<400> SEQUENCE: 5
acgcgtcgac ttattagtgg tggtggtgg                                          29

<210> SEQ ID NO 6
<211> LENGTH: 28
<212> TYPE: DNA
<213> ORGANISM: L.monocytogenes

<400> SEQUENCE: 6
ggaattccat atgaaggatg catctgca                                           28

<210> SEQ ID NO 7
<211> LENGTH: 36
<212> TYPE: DNA
<213> ORGANISM: L.monocytogenes

<400> SEQUENCE: 7
actatgatct aagtttattt ttccatctgt ataagc                                  36

<210> SEQ ID NO 8
<211> LENGTH: 36
<212> TYPE: DNA
<213> ORGANISM: L.monocytogenes

<400> SEQUENCE: 8
gcttatacag atggaaaaat aaacttagat catagt         36

<210> SEQ ID NO 9
<211> LENGTH: 51
<212> TYPE: DNA
<213> ORGANISM: L.monocytogenes

<400> SEQUENCE: 9
ggaggatacg ttgctcaatt cgaagtagcc tgggatgaag taaattatga t         51

<210> SEQ ID NO 10
<211> LENGTH: 51
<212> TYPE: DNA
<213> ORGANISM: L.monocytogenes

<400> SEQUENCE: 10
atcataattt acttcatccc aggctacttc gaattgagca acgtatcctc c         51

<210> SEQ ID NO 11
<211> LENGTH: 54
<212> TYPE: DNA
<213> ORGANISM: L.monocytogenes

<400> SEQUENCE: 11
aacatttctt gggatgaagt atcatatgac aaagaaggta acgaaattgt tcaa         54

<210> SEQ ID NO 12
<211> LENGTH: 54
<212> TYPE: DNA
<213> ORGANISM: L.monocytogenes

<400> SEQUENCE: 12
ttgaacaatt tcgttacctt ctttgtcata tgatacttca tcccaagaaa tgtt         54

<210> SEQ ID NO 13
<211> LENGTH: 51
<212> TYPE: DNA
<213> ORGANISM: L.monocytogenes

<400> SEQUENCE: 13
tatgatcctg aaggtaacga agtattaact cataaaaact ggagcgaaaa c         51

<210> SEQ ID NO 14
<211> LENGTH: 51
<212> TYPE: DNA
<213> ORGANISM: L.monocytogenes

<400> SEQUENCE: 14
gttttcgctc cagtttttat gagttaatac ttcgttacct tcaggatcat a         51

<210> SEQ ID NO 15
<211> LENGTH: 54
<212> TYPE: DNA
<213> ORGANISM: L.monocytogenes

<400> SEQUENCE: 15
aacgaaattg ttcaacataa acatgggat ggaaacaata aaagcaagct agct         54

<210> SEQ ID NO 16
<211> LENGTH: 54
<212> TYPE: DNA

<210> SEQ ID NO 16
<211> LENGTH: 54
<212> TYPE: DNA
<213> ORGANISM: L.monocytogenes

<400> SEQUENCE: 16
agctagcttg cttttattgt ttccatccca tgttttatgt tgaacaattt cgtt        54

<210> SEQ ID NO 17
<211> LENGTH: 57
<212> TYPE: DNA
<213> ORGANISM: L.monocytogenes

<400> SEQUENCE: 17
cataaaaact ggagcgaaaa ctatcaagat aaaacagctc atttcacatc gtccatc     57

<210> SEQ ID NO 18
<211> LENGTH: 57
<212> TYPE: DNA
<213> ORGANISM: L.monocytogenes

<400> SEQUENCE: 18
gatggacgat gtgaaatgag ctgttttatc ttgatagttt tcgctccagt ttttatg     57

<210> SEQ ID NO 19
<211> LENGTH: 54
<212> TYPE: DNA
<213> ORGANISM: L.monocytogenes

<400> SEQUENCE: 19
aataaaagca agctagctca ttattcaaca gtaatctatt tgcctggtaa cgcg        54

<210> SEQ ID NO 20
<211> LENGTH: 54
<212> TYPE: DNA
<213> ORGANISM: L.monocytogenes

<400> SEQUENCE: 20
cgcgttacca ggcaaataga ttactgttga ataatgagct agcttgcttt tatt        54

<210> SEQ ID NO 21
<211> LENGTH: 54
<212> TYPE: DNA
<213> ORGANISM: L.monocytogenes

<400> SEQUENCE: 21
gctcatttca catcgtccat ccctcttgaa gctaacgcga gaaatattaa tgtt        54

<210> SEQ ID NO 22
<211> LENGTH: 54
<212> TYPE: DNA
<213> ORGANISM: L.monocytogenes

<400> SEQUENCE: 22
aacattaata tttctcgcgt tagcttcaag agggatggac gatgtgaaat gagc        54

<210> SEQ ID NO 23
<211> LENGTH: 57
<212> TYPE: DNA
<213> ORGANISM: L.monocytogenes

<400> SEQUENCE: 23
cctggtaacg cgagaaatat tagaataaaa gcaagagaat gcactggttt agcttgg     57

<210> SEQ ID NO 24
<211> LENGTH: 57

```
<212> TYPE: DNA
<213> ORGANISM: L.monocytogenes

<400> SEQUENCE: 24
ccaagctaaa ccagtgcatt ctcttgcttt tattctaata tttctcgcgt taccagg          57

<210> SEQ ID NO 25
<211> LENGTH: 33
<212> TYPE: DNA
<213> ORGANISM: L.monocytogenes

<400> SEQUENCE: 25
tgggaatggt ggagagatgt aattgatgac cgg                                    33

<210> SEQ ID NO 26
<211> LENGTH: 33
<212> TYPE: DNA
<213> ORGANISM: L.monocytogenes

<400> SEQUENCE: 26
ccggtcatca attacatctc tccaccattc cca                                    33

<210> SEQ ID NO 27
<211> LENGTH: 59
<212> TYPE: DNA
<213> ORGANISM: L.monocytogenes

<400> SEQUENCE: 27
gggaatggtg gagaacggta attagtgaat atgatgttcc acttgtgaaa aatagaaat        59

<210> SEQ ID NO 28
<211> LENGTH: 59
<212> TYPE: DNA
<213> ORGANISM: L.monocytogenes

<400> SEQUENCE: 28
atttctattt ttcacaagtg gaacatcata ttcactaatt accgttctcc accattccc        59

<210> SEQ ID NO 29
<211> LENGTH: 48
<212> TYPE: DNA
<213> ORGANISM: L.monocytogenes

<400> SEQUENCE: 29
gaccggaact taccacttac aaataatata aatatctcca tctggggc                    48

<210> SEQ ID NO 30
<211> LENGTH: 48
<212> TYPE: DNA
<213> ORGANISM: L.monocytogenes

<400> SEQUENCE: 30
gccccagatg gagatattta tattatttgt aagtggtaag ttccggtc                    48

<210> SEQ ID NO 31
<211> LENGTH: 36
<212> TYPE: DNA
<213> ORGANISM: L.monocytogenes

<400> SEQUENCE: 31
agatccaggg tataaagtgg tgccccagat ggagat                                 36

<210> SEQ ID NO 32
```

-continued

```
<211> LENGTH: 36
<212> TYPE: DNA
<213> ORGANISM: L.monocytogenes

<400> SEQUENCE: 32
atctccatct ggggcaccac tttataccct ggatct                              36

<210> SEQ ID NO 33
<211> LENGTH: 39
<212> TYPE: DNA
<213> ORGANISM: L.monocytogenes

<400> SEQUENCE: 33
gaaaacaata aaagcaagac agctcatttc acatcgtcc                           39

<210> SEQ ID NO 34
<211> LENGTH: 39
<212> TYPE: DNA
<213> ORGANISM: L.monocytogenes

<400> SEQUENCE: 34
ggacgatgtg aaatgagctg tcttgctttt attgttttc                           39

<210> SEQ ID NO 35
<211> LENGTH: 33
<212> TYPE: DNA
<213> ORGANISM: L.monocytogenes

<400> SEQUENCE: 35
tttctgcaga gaaacacgcg gatgaaatcg ata                                 33

<210> SEQ ID NO 36
<211> LENGTH: 34
<212> TYPE: DNA
<213> ORGANISM: L.monocytogenes

<400> SEQUENCE: 36
aaaagagctc tctggaattg aggatgattt cttt                                34

<210> SEQ ID NO 37
<211> LENGTH: 29
<212> TYPE: DNA
<213> ORGANISM: L.monocytogenes

<400> SEQUENCE: 37
gggtcgactc ctttgattag tatattcct                                      29

<210> SEQ ID NO 38
<211> LENGTH: 22
<212> TYPE: DNA
<213> ORGANISM: L.monocytogenes

<400> SEQUENCE: 38
tttggataag cttgagcata tt                                             22

<210> SEQ ID NO 39
<211> LENGTH: 26
<212> TYPE: DNA
<213> ORGANISM: L.monocytogenes

<400> SEQUENCE: 39
gcaccaccag cagctccgcc tgcaag                                         26
```

```
<210> SEQ ID NO 40
<211> LENGTH: 26
<212> TYPE: DNA
<213> ORGANISM: L.monocytogenes

<400> SEQUENCE: 40
cttgcaggcg gagctgctgg tggtgc                                          26

<210> SEQ ID NO 41
<211> LENGTH: 30
<212> TYPE: DNA
<213> ORGANISM: L.monocytogenes

<400> SEQUENCE: 41
cccaagcttc taaagttatg gaaataagac                                      30

<210> SEQ ID NO 42
<211> LENGTH: 27
<212> TYPE: DNA
<213> ORGANISM: L.monocytogenes

<400> SEQUENCE: 42
ccgagctcac ggattttggt acttgat                                         27

<210> SEQ ID NO 43
<211> LENGTH: 3550
<212> TYPE: DNA
<213> ORGANISM: L. monocytogenes

<400> SEQUENCE: 43
gaattcttct gcttgagcgt tcatgtctca tcccccaatc gttttttatc gcccttttt      60 aaaataccct aaaaacatta ggcagtaaca acaattgtta gctgttgaaa gaaagtcacg    120
ctaaatgatg tttttttacat ataggatttt attatacaaa ttttgattcg caaaagaaat   180
gcatacatat ttaaaaacgg atttatttag atgttaaaat tgaaatagag ttagtatatg    240
gttccgaggt tgctcggaga tatactaacc ctttttgta ggaataatat atgttagttg     300
aatttattgt tttttatgat gttttttaatt gtttgttttt cggggaagtc catgattagt   360
atgcctaatc ctcgaacttt ttccgatgtt aagttgagta cgaattgctc tactttgttg   420
tttaatgctg cagcatactg acgaggtgtg aatgttaatg aagtggcgct aatatggtta   480
agaaaaagtt tattgtccgc tttggaagct tgataagcag tctggacaat ctctttgaat   540
tttgttttct cactcggacc attgtagtca tcttgaatta cttggttagg tgcgccgaac   600
tgcatgccga atttgcgtga gttaatgact aatggctttt ttgtgtggtt ctctgaaagt   660
aataatattt ttccgcggac atctttaat gtagggattt tattgctcgt gtcagttctg    720
ggagtagtgt aaaaataatc tttataaatg ttgattagtg gttggatccg ataatcaaaa   780
ctatcgttgc tgttttgctc gtcttttaaa cgcataataa tggtttcttt tggatttttc    840
tttaaaaatt gagtaatcgt ttctaataca cctgaaagtg atgcatttaa aaaaattggc    900
ccatggtaaa tgttgagatt gtcttttgct ctaatatcga tgtaccgtat tcctgcttct    960
agttgttggt acaatgacat cgtttgtgtt tgagctagtg gtttggttaa tgtccatgtt  1020
atgtctccgt tatagctcat cgtatcatgt gtacctggta tagagagcgc tgctaggttt   1080
gttgtgtcag gtagagcgga catccattgt tttgtagtta cagagttctt tattggctta  1140
ttccagttat taagcgaata tgcttttccg cctaatggga agtaaaaaa gtataaaata   1200 aaacagagta ataaaactaa tgtgcgttgc aaataattct tatacaaaat ggcccctcc   1260
```

```
tttgattagt atattcctat cttaaagtga cttttatgtt gaggcattaa catttgttaa    1320
cgacgataaa gggacagcag gactagaata aagctataaa gcaagcatat aatattgcgt    1380
ttcatcttta gaagcgaatt tcgccaatat tataattatc aaaagagagg ggtggcaaac    1440
ggtatttggc attattaggt taaaaaatgt agaaggagag tgaaacccat gaaaaaaata    1500
atgctagttt ttattacact tatattagtt agtctaccaa ttgcgcaaca aactgaagca    1560
aaggatgcat ctgcattcaa taaagaaaat tcaatttcat ccatggcacc accagcatct    1620
ccgcctgcaa gtcctaagac gccaatcgaa aagaaacacg cggatgaaat cgataagtat    1680
atacaaggat tggattacaa taaaaacaat gtattagtat accacggaga tgcagtgaca    1740
aatgtgccgc caagaaaagg ttacaaagat ggaaatgaat atattgttgt ggagaaaaag    1800
aagaaatcca tcaatcaaaa taatgcagac attcaagttg tgaatgcaat ttcgagccta    1860
acctatccag gtgctctcgt aaaagcgaat tcggaattag tagaaaatca accagatgtt    1920
ctccctgtaa aacgtgattc attaacactc agcattgatt tgccaggtat gactaatcaa    1980
gacaataaaa tcgttgtaaa aaatgccact aaatcaaacg ttaacaacgc agtaaataca    2040
ttagtggaaa gatggaatga aaaatatgct caagcttatc aaatgtaag tgcaaaaatt    2100
gattatgatg acgaaatggc ttacagtgaa tcacaattaa ttgcgaaatt tggtacagca    2160
tttaaagctg taaataatag cttgaatgta aacttcggcg caatcagtga agggaaaatg    2220
caagaagaag tcattagttt taaacaaatt tactataacg tgaatgttaa tgaacctaca    2280
agaccttcca gatttttcgg caaagctgtt actaaagagc agttgcaagc gcttggagtg    2340
aatgcagaaa atcctcctgc atatatctca agtgtggcgt atggccgtca gtttatttg    2400
aaattatcaa ctaattccca tagtactaaa gtaaaagctg cttttgatgc tgccgtaagc    2460
ggaaaatctg tctcaggtga tgtagaacta acaaatatca tcaaaaattc ttccttcaaa    2520
gccgtaattt acgaggttc cgcaaaagat gaagttcaaa tcatcgacgg caacctcgga    2580
gacttacgcg atattttgaa aaaaggcgct acttttaatc gagaaacacc aggagttccc    2640
attgcttata caacaaactt cctaaaagac aatgaattag ctgttattaa aaacaactca    2700
gaatatattg aaacaacttc aaaagcttat acagatggaa aaattaacat cgatcactct    2760
ggaggatacg ttgctcaatt caacatttct tgggatgaag taaattatga tcctgaaggt    2820
aacgaaattg ttcaacataa aaactggagc gaaaacaata aaagcaagct agctcatttc    2880
acatcgtcca tctatttgcc aggtaacgcg agaaatatta atgttacgc taaagaatgc    2940
actggtttag cttgggaatg gtggagaacg gtaattgatg accggaactt accacttgtg    3000
aaaaatagaa atatctccat ctggggcacc acgcttatc cgaaatatag taataaagta    3060
gataatccaa tcgaataatt gtaaaagtaa taaaaaatta agaataaaac cgcttaacac    3120
acacgaaaaa ataagcttgt tttgcactct tcgtaaatta ttttgtgaag aatgtagaaa    3180
caggcttatt ttttaatttt tttagaagaa ttaacaaatg taaaagaata tctgactgtt    3240
tatccatata atataagcat atcccaaagt ttaagccacc tatagtttct actgcaaaac    3300
gtataattta gttcccacat atactaaaaa acgtgtcctt aactctctct gtcagattag    3360
ttgtaggtgg cttaaactta gttttacgaa ttaaaaggga gcggtgaaat gaaaagtaaa    3420
cttatttgta tcatcatggt aatagctttt caggctcatt tcactatgac ggtaaaagca    3480
gattctgtcg gggaagaaaa acttcaaaat aatacacaag ccaaaaagac ccctgctgat    3540
ttaaaagctt                                                          3550
```

-continued

```
<210> SEQ ID NO 44
<211> LENGTH: 996
<212> TYPE: DNA
<213> ORGANISM: L. monocytogenes

<400> SEQUENCE: 44
atgtatttta tagataacaa taatgagaaa gatccacgta ttaatttagc ggtggaggaa      60
tttattttaa cagaattaaa tctggatgag cctgtgctgt tattttatat taataagcca     120
tcgattatca ttgggcgcaa ccaaaataca gtagaagaaa ttgatacaga gtatgtggag     180
aaaaatgatg tcatcgttgt gcgcagactt tctggtggcg gcgcggttta tcacgatgaa     240
ggaaacttaa atttcagttt tatcacgaaa gatgatggag agtctttcca taattttgcg     300
aaattcacac aaccgattgt ggaagctctg aaacgtttag gcgtcaatgc ggaactaaaa     360
gggcgtaatg atttattgat tgatggcttc aaagtttccg gtaatgcgca atttgcaaca     420
aaagggaaaa tgttctcaca cggaacatta atgtatgatt tgaacttaga taatgttgct     480
gcatcgctaa aaccacgtaa agataaaatc gaatcaaaag gaattaagtc tgttcgtagt     540
cgtgtagcga atatttctga tttcatggat caagaaatga caaccgagga gtttcgagat     600
ttactcttac tttatatttt tggcgtggaa aaagtagaag acgtgaaaga atacaaacta     660
actgccgcag attgggaaaa aatccacgaa atctctgcta aacgttatgg taactgggac     720
tggaattatg ggaaatcgcc aaaatttgac ttaacacgta caaaacgttt cccagttggt     780
gcagtagacg ttcgcttgaa tgtccaaaaa ggtgtgatta cagatatcaa gattttggt      840 gacttcttcg gcgttaaaaa tgtggcagat atcgaggaga aattagttaa tactacttat     900
aaacgtgaag ttttggctga ggctttagta gatatagacg taaaagaata ctttggtaat     960
attactaaag atgaattttt agatttactt tattaa                              996
```

ATTENUATED *LISTERIA SPP.* AND METHODS FOR USING THE SAME

CROSS-REFERENCE TO RELATED APPLICATIONS

This application claims priority (pursuant to 35 U.S.C. §119(e)) to the filing date of the U.S. Provisional Patent Application Ser. No. 60/385,183 filed May 29, 2002; the disclosure of which is herein incorporated by reference.

ACKNOWLEDGMENT OF GOVERNMENT SUPPORT

This invention was made with Government support under Grant Nos. AI29619 and AI27655 awarded by the National Institute of Health. The Government has certain rights in this invention.

INTRODUCTION

1. Field of the Invention

The field of this invention is *Listeria* species, e.g., *Listeria monocytogenes*, particularly recombinant strains of *Listeria* species, and methods for their construction and use.

2. Background of the Invention

The use of vaccines is a cost-effective medical tool for the management of infectious diseases, including infectious diseases caused by bacteria, viruses, parasites, and fungi. In addition to effecting protection against infectious diseases, effort is also being expended to develop vaccines that stimulate the host's immune system to intervene in tumor growth.

Host immune responses include both the humoral immune response involving antibody production and the cell-mediated immune response. Protective immunization via vaccine has usually been designed to induce the formation of humoral antibodies directed against infectious agents, tumor cells, or the action of toxins. However, the control of certain diseases characterized by the presence of tumor cells or by chronic infection of cells with infectious agents, often requires a cell-mediated immune response either in place of, or in addition to the generation of antibody. While the humoral immune response may be induced using live infectious agents and agents that have been inactivated, a cellular immune response is most effectively induced through the use of live agents as vaccines. Such live agents include live infectious agents which may gain access to the cytoplasm of host cells where the proteins encoded by these agents are processed into epitopes which when presented to the cellular immune system, induce a protective response.

Microorganisms, particularly *Salmonella* and *Shigella*, which have been attenuated using a variety of mechanisms have been examined for their ability to encode and express heterologous antigens. Such bacteria may be useful as live attenuated bacterial vaccines which serve to induce a cellular immune response directed against a desired heterologous antigen.

*Listeria monocytogenes* is a Gram-positive, food-borne human and animal pathogen responsible for serious infections in immunocompromised individuals and pregnant women. Severe *L. monocytogenes* infections in humans are characterized by meningitis, meningoencephalitis, septicemia, and fetal death. *L. monocytogenes* is ubiquitous in nature and, in addition, can be isolated from a wide variety of warm-blooded animals. *L. monocytogenes* elicits a predominantly cellular immune response when inoculated into an animal.

As such, *L. monocytogenes* has been employed as a vector for a variety of different applications. When used as a vector for the transmission of genes encoding heterologous antigens derived from infectious agents or derived from tumor cells, recombinant *Listeria* encoding and expressing an appropriate heterologous antigen have been shown to successfully protect mice against challenge by lymphocytic choriomeningitis virus (Shen et al., 1995, Proc. Natl. Acad. Sci. USA 92:3987-3991; Goossens et al., 1995, Int. Immunol. 7:797-802) and influenza virus (Ikonomidis et al., 1997, Vaccine 15:433-440). Furthermore, model tumor antigen-expressing recombinant *Listeria* have been used to protect mice against lethal tumor cell challenge (Pan et al., 1995, Nat. Med. 1:471-477; Paterson and Ikonomidis, 1996, Curr. Opin. Immunol. 8:664-669, Gunn et al., 2001 J. Immunol. 167:6471-6479). In addition, it is known that a strong cell-mediated immune response directed against HIV-1 gag protein may be induced in mice infected with a recombinant *L. monocytogenes* comprising HIV-1 gag (Frankel et al., 1995, J. Immunol. 155:4775-4782, Friedman et al., 2000 J. Virol. 74:9987-9993).

As demonstrated in a significant body of published literature (ibid) related to the application of *Listeria* as a vaccine vector for the prevention and treatment of infectious disease and cancer, this bacterial-based vector has significant advantages over other recombinant vaccine delivery systems. However, safety concerns regarding the use in vivo of this bacterial vaccine vector remain an important issue. The use of the most common wild-type strain of *Listeria, L. monocytogenes*, can be accompanied by severe side effects, including the development of listeriosis in the inoculated animal. This disease, which is normally food-borne, is characterized by meningitis, septicemia, abortion and often a high rate of mortality in infected individuals. While natural infections by *L. monocytogenes* are fairly rare and may be readily controlled by a number of antibiotics, the organism may nevertheless be a serious threat in immunocompromised or pregnant patients.

Thus, for broad application to vaccines against infectious and malignant disease, there is an essential requirement for the development of attenuated strains of *L. monocytogenes*.

Relevant Literature

Patents and published patent applications of interest include: U.S. Pat. Nos. 4,816,253; 5,830,702; 6,051,237 and 6,099,848; as well as published PCT application serial no.: WO 99/25376 and WO 00/09733.

SUMMARY OF THE INVENTION

Attenuated *Listeria* bacteria are provided. The subject bacteria are characterized by having a mutation in a gene chosen from the IpIA gene and the hly gene. The subject bacteria find use in a variety of applications, where representative applications of interest include, but are not limited to: (a) use of the subject bacteria as adjuvants; (b) use of the subject bacteria as delivery vectors for introducing macromolecules into a cell; (c) use of the subject bacteria as vaccines for eliciting or boosting a cellular immune response; etc.

DESCRIPTION OF THE SPECIFIC EMBODIMENTS

Figure 1:
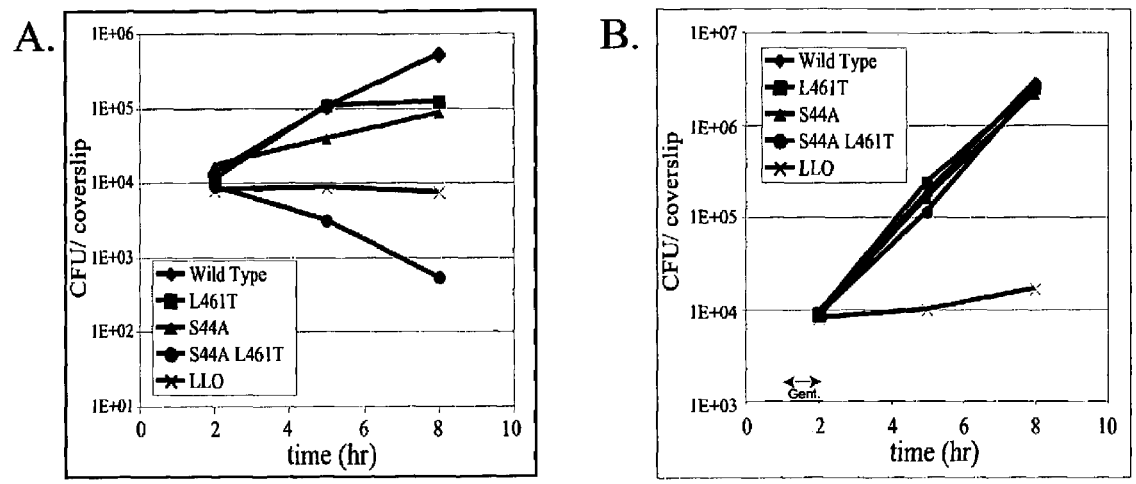
FIGS. 1A and 1B. The LLO Mutants Permeabilize the Plasma Membrane C57BL/6 bone-marrow-derived macrophages were infected for 4 hours without gentamicin then stained with the membrane impermeant dye propidium iodide, which increases fluorescence when it passes through the membrane and interacts with host DNA. $2.5 \times 10^4$ cells were examined by flow cytometry, half of which are displayed. The gray-shaded histogram represents uninfected cells. The fluorescence range of cells scored as permeabilized, indicated by the marker M1, was defined by adding $10^6$ hemolytic units of purified LLO L461T to the macrophages, and displayed in 1A. The infecting strain and the percentage of cells falling within marker M1 are indicated.

Attenuated *Listeria* bacteria are provided. The subject bacteria are characterized by having a mutation in a gene chosen from the IplA gene and the hly gene. The subject bacteria find use in a variety of applications, where representative applications of interest include, but are not limited to: (a) use of the subject bacteria as adjuvants; (b) use of the subject bacteria as delivery vectors for introducing macromolecules into a cell; (c) use of the subject bacteria as vaccines for eliciting or boosting an antigen-specific humoral or cellular immune response; etc.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing various invention components that are described in the publications that might be used in connection with the presently described invention.

In further describing the subject invention, the subject attenuated bacteria are reviewed first in greater detail, followed by a review of representative applications in which the subject vectors and methods find use.

Attenuated *Listeria* Bacteria

As summarized above, the subject invention provides attenuated *Listeria* bacteria. The term "attenuated," as used herein, describes the diminution in the ability of the subject bacteria to cause disease in an animal as a whole, e.g., as measured by the $LD_{50}$ of the bacteria, as described below. More specifically, the pathogenic characteristics of the attenuated *Listeria* strain, as viewed from the vantage of the host animal as a whole (as opposed to a cell based perspective) have been lessened compared with wild-type *Listeria*, although the attenuated *Listeria* is capable of growth and maintenance in culture. In certain embodiments, bacteria are considered to be attenuated if, upon the intravenous inoculation of Balb/c mice (as described in the experimental section, below), the lethal dose at which 50% of inoculated animals survive ($LD_{50}$) is increased above the $LD_{50}$ of wild-type *Listeria* by at least about 10-fold, such as by at least about 100-fold, including by at least about 1,000 fold, where in certain embodiments the magnitude of increase is at least about 10,000 fold, such as at least about 100,000-fold, as determined using the assay employed in the experimental section below. An attenuated strain of *Listeria* according to the subject invention is thus one which does not kill an animal to which it is administered, or is one which kills the animal only when the number of bacteria administered is vastly greater than the number of wild type non-attenuated bacteria which would be required to kill the same animal.

In certain embodiments, attenuated species according to the subject invention are ones that exhibit a decreased virulence compared to their corresponding wild type strain in the Competitive Index Assay as described in Auerbach et al., "Development of a Competitive Index Assay To Evaluate the Virulence of *Listeria monocytogenes* actA Mutants during Primary and Secondary Infection of Mice," Infection and Immunity, September 2001, p. 5953-5957, Vol. 69, No. 9. In this assay, mice are inoculated with test and reference, e.g., wild-type, strains of bacteria. Following a period of time, e.g., 48 to 60 hours, the inoculated mice are sacrificed and one or more organs, e.g., liver, spleen, are evaluated for bacterial abundance. In these embodiments, a given bacterial strain is considered to be less virulent if its abundance in the spleen is at least about 50-fold, or more, such as 70-fold or more less than that observed with the corresponding wild-type strain, and/or its abundance in the liver is at least about 10-fold less, or more, such as 20-fold or more less than that observed with the corresponding wild-type strain.

In yet other embodiments, bacteria are considered to be less virulent if they show abortive replication in less than about 8 hours, such as less than about 6 hours, including less than about 4 hours, as determined using the assay described in Jones and Portnoy, Intracellular growth of bacteria. (1994b) *Methods Enzymol.* 236:463-467. In yet other embodiments, bacteria are considered to be attenuated or less virulent if, compared to wild-type, they form smaller plaques in the plaque assay employed in the Experimental Section, below, where cells, such as murine L2 cells, are grown to confluency, e.g., in six-well tissue culture dishes, and then infected with bacteria. Subsequently, DME-agar containing gentamicin is added and plaques are grown for a period of time, e.g., 3 days. Living cells are then visualized by adding an additional DME-agar overlay, e.g., containing neutral red (GIBCO BRL) and incubated overnight. In such an assay, the magnitude in reduction in plaque size observed with the attenuated mutant as compared to the wild-type is, in certain embodiments, 10%, including 15%, such as 25% or more.

The subject bacteria may be any *Listeria* species that is rendered attenuated according to the subject invention. Thus, strains of *Listeria* other than *L. monocytogenes* may be used for the generation of attenuated mutants according to the present invention. In certain embodiments, the *Listeria* strain is *L. monocytogenes*.

In certain embodiments, the subject bacteria are cytotoxic. A particular strain of bacteria is considered to be cytotoxic if it compromises its host cell in a period of less than about 8 hours, sometimes less than about 6 hours, e.g., in less than about 5 hours, less than about 4 hours, less than about 3 hours, less than about two hours, or less than about 1 hour, as determined using the cytotoxicity assay described below. Representative cytotoxic bacterial strains according to the subject invention include those hly mutant stains described below.

In certain embodiments, the subject bacteria comprise a mutated hly gene, by which is meant that the bacteria comprise an hly gene where the coding sequence of the gene has been altered to encode an LLO product whose amino acid sequence differs from wild type LLO by at least one residue, e.g, by missing the at least one residue, by having a substitute for at least one residue, etc. In certain embodiments, the encoded product is a deletion mutant, by which is meant that one or more residues found in the wild type protein are absent or missing in the mutant polypeptide, where the missing residues are not replaced by substitute residues. In other embodiments, the encoded product is a point mutant, by which is meant that one or more residues of the wild type protein, which may or may not be adjacent to one another, are substituted with a different residue.

In certain embodiments, the mutant hly gene is one that encodes a mutant LLO product that has more hemolytic activity at neutral pH than the wild type LLO protein, where the hemolyticity is determined using the assay described in Glomski et al., J. Cell Biol. (Mar. 18, 2002) 156:1029-1038 and the Experimental Section, below. As measured by this assay, the encoded mutant LLO protein of the bacteria of these embodiments is at least about 2-fold, sometimes at least about 5-fold and sometimes at least about 10-fold more hemolytic than the wild type LLO protein. In certain of these embodiments, the mutation of the hly gene is one that encodes a point mutant product, such that one or more residues in the encoded product differs from the corresponding residue in the wild type protein. In certain of these embodiments, a residue falling between 450 and 470, often between 455 and 465 is substituted, where in certain embodiments the substituted residue is residue 461. In these embodiments, the L at position 461 is substituted with a non-L residue, where the substituting residue may be T, N, Q, S etc, but is T in certain embodiments. In certain embodiments, the mutation is found in domain 3, or a residue that interacts with a residue in domain 3.

In certain embodiments, the mutant hly gene includes a mutation in the PEST-like sequence encoding domain of the gene. The PEST-like sequence of the encoded product is found in the N-terminal 75 residues of the LLO protein, and more specifically in the N-terminal 60 residues of the LLO protein, and more precisely between residues 34 and 59. The mutation of the PEST-like sequence encoding domain may be one that encodes a deletion mutant product or a point mutation product.

In certain embodiments, mutation of the PEST-like sequence encoding domain is one that disrupts a potential mitogen activated, protein kinase (MAPK) phosphorylation site within the PEST-like sequence. In certain of these embodiments, the mutation is one that encodes a point mutant at a residue from position 30 and 60. In certain embodiments, the residue that is substituted in the encoded mutant product is residue 44. In these certain embodiments, the S at position 44 is substituted with a non-S residue, where the substituting residue may be A, G, I, F, C, L, M, V, etc, but is A in certain embodiments. In certain embodiments, the mutation is one that provides for more of the protein being produced. As such, in these embodiments there may not be a codon mutation that results in an altered residue, such as S44A, but instead results in a codon selection that provides for more RNA as compared to wildtype, and therefore ultimately more protein.

In certain embodiments, the mutation of the PEST-like sequence-encoding domain is one that provides for a deletion of at least a portion of, if not all of, the residues that make up the PEST-like sequence. Thus, the mutation may be a deletion of one or more residues, including all of the residues, from about 30 to about 60, e.g., a deletion of residues 34 to 59. In certain embodiments, however, the attenuated bacteria of interest are not bacteria in which the entire PEST-like sequence has been deleted from the encoded LLO product, such as the bacteria reported in Decatur et al., Science (2000) 290:992-995.

In certain embodiments, the subject attenuated bacteria have only a single type of hly mutation, as described above. In yet other embodiments, the bacteria have two or more of the specific hly mutations, as described above.

Specific attenuated bacteria of interest that include a mutated hly gene include, but are not limited to: DP-L4017; DP-L4057, DP-L4384; DP-L4038 and DP-L4042, where these specific strains are described below in greater detail. DP-L4017 and DP-L4038are deposited with the American Type Culture Collection depository (10801University Boulevard, Manassas, Va. 20110-2209) and have been assigned ATCC accession nos. PTA-5235 and PTA-5236, respectively.

In certain embodiments, the attenuated bacteria include a mutated IpIA gene, where the mutation is one that results in an attenuated bacteria, as described above. In many embodiments, the attenuated bacteria display no defects in vegetative growth under typical *Listeria* culture conditions, but with the mutated IpIA gene exhibit abortive replication a certain period of time, e.g., 2 hours, usually 4 hours, following infection, as determined using an assay to measure bacterial intracellular growth within infected J774 macrophages (ATCC #TIB-67), as described in Glomski et al., 2002 J. Cell Biol. 156:1029-1038); and form smaller plaques than wild type strains in an assay for growth and cell to cell spread in the murine L2 cell line, as described in the Experimental Section, infra, where the smaller plaques are typically at least about 50 fold smaller, sometimes at least about 100 fold smaller and sometimes undetectable as compared to those produced by wild type bacteria in the same assay.

In certain embodiments, the IpIA mutation is a mutation that results in an IpIA gene that no longer encodes a product. In other embodiments where the IpIA mutated gene still encodes a product, the encoded product is a deletion mutant, by which is meant that one or more residues found in the wild type protein are absent or missing in the mutant polypeptide. In certain embodiments, the percentage of residues that are deleted may be 10, 20, 30, 40, 50, 60, 70, 80, or 90% by number or more of the residues. In other embodiments, the encoded product is a point mutant, by which is meant that one or more residues of the wild type protein, which may or may not be adjacent to one another, are substituted with a different residue.

A specific representative attenuated bacteria having a mutated IpIA gene is DP-L4364, as described in the Experimental Section, below, in greater detail. DP-L4364is deposited with the American Type Culture Collection depository (10801 University Boulevard, Manassas, Va. 20110-2209) and has been assigned ATCC accession no. PTA-5237.

The above-attenuated bacteria may be fabricated using a variety of different protocols. As such, generation of the subject attenuated bacteria may be accomplished in a number of ways that are well known to those of skill in the art, including deletion mutagenesis, insertion mutagenesis, and mutagenesis which results in the generation of frameshift mutations, mutations which effect premature termination of a protein, or mutation of regulatory sequences which affect gene expression. Mutagenesis can be accomplished using recombinant DNA techniques or using traditional mutagenesis technology using mutagenic chemicals or radiation and subsequent selection of mutants. Representative protocols of different ways to generate attenuated bacteria according to the present invention are provided in the Experimental Section, below.

In certain embodiments, attenuated bacteria according to the subject invention express a heterologous antigen. The heterologous antigen is, in certain embodiments, one that is capable of providing protection in an animal against challenge by the infectious agent from which the heterologous antigen was derived, or which is capable of affecting tumor growth and metastasis in a manner which is of benefit to a host organism. Heterologous antigens which may be introduced into a *Listeria* strain of the subject invention by way of DNA encoding the same thus include any antigen which when expressed by *Listeria* serves to elicit a cellular immune response which is of benefit to the host in which the response is induced. Heterologous antigens therefore include those specified by infectious agents, wherein an immune response directed against the antigen serves to prevent or treat disease caused by the agent. Such heterologous antigens include, but are not limited to, viral, bacterial, fungal or parasite surface proteins and any other proteins, glycoproteins, lipoprotein, glycolipids, and the like. Heterologous antigens also include those which provide benefit to a host organism which is at risk for acquiring or which is diagnosed as having a tumor that expresses the said heterologous antigen(s). The host organism is preferably a mammal and most preferably, is a human.

By the term "heterologous antigen," as used herein, is meant a protein or peptide, a glycoprotein or glycopeptide, a lipoprotein or lipopeptide, or any other macromolecule which is not normally expressed in *Listeria*, which substantially corresponds to the same antigen in an infectious agent, a tumor cell or a tumor-related protein. The heterologous antigen is expressed by a strain of *Listeria* according to the subject invention, and is processed and presented to cytotoxic T-cells upon infection of mammalian cells by the strain. The heterologous antigen expressed by *Listeria* species need not precisely match the corresponding unmodified antigen or protein in the tumor cell or infectious agent so long as it results in a T-cell response that recognizes the unmodified antigen or protein which is naturally expressed in the mammal. In other examples, the tumor cell antigen may be a mutant form of that which is naturally expressed in the mammal, and the antigen expressed by the *Listeria* species will conform to that tumor cell mutated antigen. By the term "tumor-related antigen," as used herein, is meant an antigen which affects tumor growth or metastasis in a host organism. The tumor-related antigen may be an antigen expressed by a tumor cell, or it may be an antigen which is expressed by a non-tumor cell, but which when so expressed, promotes the growth or metastasis of tumor cells. The types of tumor antigens and tumor-related antigens which may be introduced into *Listeria* by way of incorporating DNA encoding the same, include any known or heretofore unknown tumor antigen. In other examples, the "tumor-related antigen" has no effect on tumor growth or metastasis, but is used as a component of the *Listeria* vaccine because it is expressed specifically in the tissue (and tumor) from which the tumor is derived. In still other examples, the "tumor-related antigen" has no effect on tumor growth or metastasis, but is used as a component of the *Listeria* vaccine because it is selectively expressed in the tumor cell and not in any other normal tissues.

The heterologous antigen useful in vaccine development may be selected using knowledge available to the skilled artisan, and many antigenic proteins which are expressed by tumor cells or which affect tumor growth or metastasis or which are expressed by infectious agents are currently known. For example, viral antigens which may be considered as useful as heterologous antigens include but are not limited to the nucleoprotein (NP) of influenza virus and the gag protein of HIV. Other heterologous antigens include, but are not limited to, HIV env protein or its component parts gp120 and gp41, HIV nef protein, and the HIV pol proteins, reverse transcriptase and protease. Still other heterologous antigens can be those related to hepatitis C virus (HCV), including but not limited to the E1 and E2 glycoproteins, as well as non-structural (NS) proteins, for example NS3. In addition, other viral antigens such as herpes virus proteins may be useful. The heterologous antigens need not be limited to being of viral origin. Parasitic antigens, such as, for example, malarial antigens, are included, as are fungal antigens, bacterial antigens and tumor antigens.

As noted herein, a number of proteins expressed by tumor cells are also known and are of interest as heterologous antigens which may be inserted into the vaccine strain of the invention. These include, but are not limited to, the bcr/abl antigen in leukemia, HPVE6 and E7 antigens of the oncogenic virus associated with cervical cancer, the MAGE1 and MZ2-E antigens in or associated with melanoma, and the MVC-1 and HER-2 antigens in or associated with breast cancer. Other coding sequences of interest include, but are not limited to: costimulatory molecules, immunoregulatory molecules, and the like.

The introduction of DNA encoding a heterologous antigen into a strain of *Listeria* may be accomplished, for example, by the creation of a recombinant *Listeria* in which DNA encoding the heterologous antigen is harbored on a vector, such as a plasmid for example, which plasmid is maintained and expressed in the *Listeria* species, and in whose antigen expression is under the control of prokaryotic promoter/regulatory sequences. Alternatively, DNA encoding the heterologous antigen may be stably integrated into the *Listeria* chromosome by employing, for example, transposon mutagenesis, homologous recombination, or integrase mediated site-specific integration (as described in application Ser. No. 10/136,860, the disclosure of which is herein incorporated by reference).

Several approaches may be employed to express the heterologous antigen in *Listeria* species as will be understood by one skilled in the art once armed with the present disclosure. In certain embodiments, genes encoding heterologous antigens are designed to either facilitate secretion of the heterologous antigen from the bacterium or to facilitate expression of the heterologous antigen on the *Listeria* cell surface.

In certain embodiments, a fusion protein which includes the desired heterologous antigen and a secreted or cell surface protein of *Listeria* is employed. Listerial proteins which are suitable components of such fusion proteins include, but are not limited to, listeriolysin O (LLO) and phosphatidylinositol-specific phospholipase (PI—PLC). A fusion protein may be generated by ligating the genes which encode each of the components of the desired fusion protein, such that both genes are in frame with each other. Thus, expression of the ligated genes results in a protein comprising both the heterologous antigen and the listerial protein. Expression of the ligated genes may be placed under the transcriptional control of a listerial promoter/regulatory sequence such that expression of the gene is effected during growth and replication of the organism. Signal sequences for cell surface expression and/or secretion of the fused protein may also be added to genes encoding heterologous antigens in order to effect cell surface expression and/or secretion of the fused protein. When the heterologous antigen is used alone (i.e., in the absence of fused *Listeria* sequences), it may be advantageous to fuse thereto signal sequences for cell surface expression and/or secretion of the heterologous antigen. The procedures for accomplishing this are well know in the art of bacteriology and molecular biology.

The DNA encoding the heterologous antigen which is expressed is, in many embodiments, preceded by a suitable promoter to facilitate such expression. The appropriate promoter/regulatory and signal sequences to be used will depend on the type of listerial protein desired in the fusion protein and will be readily apparent to those skilled in the art of *Listeria* molecular biology. For example, preferred *L. monocytogenes* promoter/regulatory and/or signal sequences which may be used to direct expression of a fusion protein include, but are not limited to, sequences derived from the *Listeria* hly gene which encodes LLO, the *Listeria* p60 (iap) gene, and the *Listeria* actA gene which encodes a surface protein necessary for *L. monocytogenes* actin assembly. Other promoter sequences of interest include the plcA gene which encodes PI-PLC, the *Listeria* mpI gene, which encodes a metalloprotease, and the *Listeria* inlA gene which encodes internalin, a *Listeria* membrane protein. The heterologous regulatory elements such as promoters derived from phage and promoters or signal sequences derived from other bacterial species may be employed for the expression of a heterologous antigen by the *Listeria* species.

In certain embodiments, the attenuated *Listeria* include a vector. The vector may include DNA encoding a heterologous antigen. Typically, the vector is a plasmid that is capable of replication in *Listeria*. The vector may encode a heterologous antigen, wherein expression of the antigen is under the control of eukaryotic promoter/regulatory sequences, e.g., is present in an expression cassette. Typical plasmids having suitable promoters that are of interest include, but are not limited to, pCMVbeta comprising the immediate early promoter/enhancer region of human cytomegalovirus, and those which include the SV40 early promoter region or the mouse mammary tumor virus LTR promoter region.

As such, in certain embodiments, the subject bacteria include at least one coding sequence for heterologous polypeptide/protein, as described above. In many embodiments, this coding sequence is part of an expression cassette, which provides for expression of the coding sequence in the *Listeria* cell for which the vector is designed. The term "expression cassette" as used herein refers to an expression module or expression construct made up of a recombinant DNA molecule containing at least one desired coding sequence and appropriate nucleic acid sequences necessary for the expression of the operably linked coding sequence in a particular host organism, i.e., the *Listeria* cell for which the vector is designed, such as the promoter/regulatory/signal sequences identified above, where the expression cassette may include coding sequences for two or more different polypeptides, or multiple copies of the same coding sequence, as desired. The size of the coding sequence and/or expression cassette that includes the same may vary, but typically falls within the range of about 25-30 to about 6000 bp, usually from about 50 to about 2000 bp. As such, the size of the encoded product may vary greatly, and a broad spectrum of different products may be encoded by the expression cassettes present in the vectors of this embodiment.

As indicated above, the vector may include at least one coding sequence, where in certain embodiments the vectors include two or more coding sequences, where the coding sequences may encode products that act concurrently to provide a desired results. In general, the coding sequence may encode any of a number of different products and may be of a variety of different sizes, where the above discussion merely provides representative coding sequences of interest.

Utility

The above-described attenuated bacteria find use in a number of different applications. Representative uses of the subject bacteria include, but are not limited to: (a) immunogens for generating antibodies to Listeria spp.; (b) adjuvant compositions in immunizing protocols; (c) vectors for introducing macromolecules, e.g., nucleic acids or proteins, into the cytoplasm of target cells; and (d) vaccine compositions, e.g., for eliciting or boosting a cellular immune response in a host. Each of these representative applications is now further described separately below. Uses for attenuated Listeria spp. are also described in U.S. Pat. No. 6,099,848; the disclosure of which is herein incorporated by reference, where the subject attenuated bacteria find use in the applications described in this U.S. Patent.

Generation of Listeria Specific Antibodies

The subject attenuated bacteria find use in the generation of antibodies specific for Listeria spp. In these applications, the attenuated bacteria are administered to a suitable host according to known techniques, and resultant antibodies are harvested from the immunized host. Immunization can be carried out in a variety of ways with a number of different animals. Host animals of interest include rabbits, mice, rats, goats and sheep, etc. Any mammal capable of immune response can be employed as the host animal in antibody production. For the most part for commercial production of antibodies, relatively large animals are employed, such as equine, bovine, porcine, canine, ovine, caprine, rodentia, rabbits and hares. A representative antibody production protocol in which the subject attenuated bacteria may be employed includes the antibody generation protocol as described in U.S. Pat. No. 4,816,253; the disclosure of which is herein incorporated by reference.

Adjuvant Compositions

The subject attenuated bacterial strains also find use as immunopotentiating agents, i.e., as adjuvants. In such applications, the subject attenuated bacteria may be administered in conjunction with an immunogen, e.g., a tumor antigen, modified tumor cell, etc., according to methods known in the art where live bacterial strains are employed as adjuvants. See, e.g., Berd et al., Vaccine 2001 Mar. 21;19(17-19):2565-70.

In some embodiments, the attenuated bacterial strains are employed as adjuvants by chemically coupled to a sensitizing antigen. The sensitizing antigen can be any antigen of interest, where representative antigens of interest include, but are not limited to: viral agents, e.g., Herpes simplex virus; malaria parasite; bacteria, e.g., staphylococcus aureus bacteria, diphtheria toxoid, tetanus toxoid, shistosomula; tumor cells, e.g. $CAD_2$ mammary adenocarcinomia tumor cells, and hormones such as thyroxine $T_4$, triiiodothyronine $T_3$, and cortisol. The coupling of the sensitizing antigen to the immunopotentiating agent can be accomplished by means of various chemical agents having two reactive sites such as, for example, bisdiazobenzidine, glutaraldehyde, di-iodoacetate, and diisocyanates, e.g., m-xylenediisocyanate and toluene-2, 4-diisocyanate. Use of Listeria spp. as adjuvants is further described in U.S. Pat. No. 4,816,253; the disclosure of which is herein incorporated by reference.

Delivery Vehicles

The subject attenuated bacteria also find use as vectors or delivery vehicles for delivery of macromolecules into target cells, e.g., as described in: PCT publication no. WO 00/09733 (the priority application of which is herein incorporated by reference); and Dietrich et al., Nature Biotechnology (1998) 16: 181-185. A variety of different types of macromolecules may be delivered, including, but not limited to: nucleic acids, polypeptides/proteins, etc., as described in these publications.

Vaccines

The subject attenuated bacteria also find use as vaccines. The vaccines of the present invention are administered to a vertebrate by contacting the vertebrate with a sublethal dose of the attenuated Listeria vaccine, where contact typically includes administering the vaccine to the host. In many embodiments, the attenuated bacteria are provided in a pharmaceutically acceptable formulation. Administration can be oral, parenteral, intranasal, intramuscular, intradermal, intraperitoneal, intravascular, subcutaneous, direct vaccination of lymph nodes, administration by catheter or any one or more of a variety of well-known administration routes. In farm animals, for example, the vaccine may be administered orally by incorporation of the vaccine in feed or liquid (such as water). It may be supplied as a lyophilized powder, as a frozen formulation or as a component of a capsule, or any other convenient, pharmaceutically acceptable formulation that preserves the antigenicity of the vaccine. Any one of a number of well known pharmaceutically acceptable diluents or excipients may be employed in the vaccines of the invention. Suitable diluents include, for example, sterile, distilled water, saline, phosphate buffered solution, and the like. The amount of the diluent may vary widely, as those skilled in the art will recognize. Suitable excipients are also well known to those skilled in the art and may be selected, for example, from A. Wade and P. J. Weller, eds., Handbook of Pharmaceutical Excipients (1994) The Pharmaceutical Press: London. The dosage administered may be dependent upon the age, health and weight of the patient, the type of patient, and the existence of concurrent treatment, if any. The vaccines can be employed in dosage forms such as capsules, liquid solutions, suspensions, or elixirs, for oral administration, or sterile liquid for formulations such as solutions or suspensions for parenteral, intranasal intramuscular, or intravascular use. In accordance with the invention, the vaccine may be employed, in combination with a pharmaceutically acceptable diluent, as a vaccine composition, useful in immunizing a patient against infection from a selected organism or virus or with respect to a tumor, etc. Immunizing a patient means providing the patient with at least some degree of therapeutic or prophylactic immunity against selected pathogens, cancerous cells, etc.

The subject vaccines find use in methods for eliciting or boosting a cellular immune response, e.g., a helper T cell or a cytotoxic T-cell response to a selected agent, e.g., pathogenic organism, tumor, etc., in a vertebrate, where such methods include administering an effective amount of the Listeria vaccine. The subject vaccines find use in methods for eliciting in a vertebrate an innate immune response that augments the antigen-specific immune response. Furthermore, the vaccines of the present invention may be used for treatment post-exposure or post diagnosis. In general, the use of vaccines for post-exposure treatment would be recognized by one skilled in the art, for example, in the treatment of rabies and tetanus. The same vaccine of the present invention may be used, for example, both for immunization and to boost immunity after exposure. Alternatively, a different vaccine of the present invention may be used for post-exposure treatment, for example, such as one that is specific for antigens expressed in later stages of exposure. As such, the subject vaccines prepared with the subject vectors find use as both prophylactic and therapeutic vaccines to induce immune responses that are specific for antigens that are relevant to various disease conditions.

The patient may be any human and non-human animal susceptible to infection with the selected organism. The subject vaccines will find particular use with vertebrates such as man, and with domestic animals. Domestic animals include domestic fowl, bovine, porcine, ovine, equine, caprine, Leporidate (such as rabbits), or other animal which may be held in captivity.

In general, the subject vaccines find use in vaccination applications as described U.S. Pat. Nos. 5,830,702 and 6,051, 237, the disclosure of which is herein incorporated by reference; as well as PCT publication no WO 99/25376, the disclosures of the priority applications of which are herein incorporated by reference.

The following examples are offered by way of illustration and not by way of limitation.

EXPERIMENTAL

I. Generation and Characterization of DP-L4017

A. Materials and Methods

1. Bacterial Strains, Growth Conditions, and Reagents

The wild-type $L.$ $monocytogenes$ strain used for these studies was 10403S. $L.$ $monocytogenes$ strains with deletions of actA were constructed by allelic exchange as described previously (Skoble, J., D. A. Portnoy, and M. D. Welch. 2000. Three regions within ActA promote Arp2/3 complex-mediated actin nucleation and $Listeria$ $monocytogenes$ motility. $J.$ $Cell$ $Biol.$ 150:527-538.) The $L.$ $monocytogenes$ strain with an in-frame deletion of PI-PLC (ΔplcA, or DP-L1552) and strain ActA GGG (DP-L4032) were previously described (Camilli, A., L. G. Tilney, and D. A. Portnoy. 1993. Dual roles of plcA in $Listeria$ $monocytogenes$ pathogenesis. $Mol.$ $Microbiol.$ 8:143-157; Skoble et al., 2002, supra). The merodiploid hly strain (DP-L4076) will be published in a subsequent manuscript (Lauer, P., M. Y. N. Chow, M. J. Loessner, D. A. Portnoy, and R. Calendar. "Construction, characterization and use of two $Listeria$ $monocytogenes$ site-specific integration vectors," J Bacteriol. August 2002; 184(15):4177-86.). $E.$ $coli$ strains DH5α (GIBCO BRL) or XL-1 Blue (Stratagene) were used for cloning. $E.$ $coli$ strains BL21 (DE3) or BL21 (DE3) PlysS (Stratagene) were used for expression of proteins from pET vectors.

$L.$ $monocytogenes$ was grown in 3 ml brain heart infusion broth (BHI; Becton Dickinson) slanted without agitation in 15 ml conical tubes at 30° C. overnight, unless otherwise noted. All $E.$ $coli$ strains were grown in Luria-Bertani broth (LB; Becton Dickinson) at 37° C. shaking, unless otherwise noted. All tissue culture cells were grown in DME (GIBCO BRL), containing 7.5% heat-deactivated FBS (Hy-Clone) and 2 mM glutamine (DME; GIBCO BRL), at 37° C. and 5% $CO_2$, unless otherwise noted. All chemicals were purchased from Sigma-Aldrich, unless otherwise noted.

B. Sequences

The GenBank/EMBL/DDBJ accession nos. for the proteins examined in this study are the following: LLO, M29030 (SEQ ID NO 43); PFO, M36704; ivanolysin O, X60461; seeligeriolysin O, X60462; streptolysin O, M18638; pneumolysin, X52474; cereolysin, D21270; alveolysin, M62709; suilysin, Z36907; and pyolysin, U84782.

C. Cloning

1. Construction of the LLO expression vector

DNA and protein analysis was performed using MacVector software (Genetics Computer Group). The region of hly coding for mature LLO was amplified by PCR, with the primers and templates as described in Table III using Vent polymerase (New England Biolabs, Inc.) to introduce a six histidine tag. The amplified fragment was then cut with restriction enzymes and ligated into pET29b (Novagen). This plasmid and all other plasmids were initially cloned in $E.$ $coli$ strain XL-1 Blue and then transferred into $E.$ $coli$ expression strain BL21 (DE3), unless otherwise noted, to yield strain DP-3570.

TABLE III

| Number | Sequence 5'→3' (including enzyme site)* | | Construct |
|---|---|---|---|
| 3140 | GGAATTCCATATGAAGGATGCATCTGCATTCAAT (NdeI) | SEQ ID NO:01 | His-LLO, P3570 |
| 3232 | CGGGATCCTTATTAGTGGTGGTGCTGGTGGTGTTCGATTGGA TTATCTAC (BamH1) | SEQ ID NO:02 | His-LLO, p3570 |
| 3541 | GGAATTCCCATGGGAAAGGATATAACAGATAAAAATCA (Nco1) | SEQ ID NO:03 | His-PFO, p4167 |
| 3542 | CGGGATCCTTATTAGTGGTGGTOGTGGTGGTGATTGTAAGTA ATACTAGATCCA (BamH1) | SEQ ID NO:04 | His-PFO, p4167 |
| 3543 | ACGCGTCGACTTATTAGTGGTGGTGGTGO (Sal1) | SEQ ID NO:05 | His-LLO (1-3) PFO4 |
| 3575 | GGAATTCCATATGAAGGATGCATCTGCA (Nde1) | SEQ ID NO:06 | His-LLO (1-3) PFO4 |
| 3578 | ACTATGATCTAAGTTTATTTTTCCATCTGTATAAGC | SEQ ID NO:07 | His-LLO (1-3) PFO4 |
| 3579 | GCTTATACAGATGGAAAAATAAACTTAGATCATAGT | SEQ ID NO:08 | His-LLO (1-3) PFO4 |
| 3740 | GGAGGATACGTTGCTCAATTCGAAGTAGCCTGGGATGAAGTA AATTATGAT | SEQ ID NO:09 | Chimera 1 |
| 3741 | ATCATAATTTACTTCATCCCAGGCTACTTCGAATTGAGCAAC GTATCCTCC | SEQ ID NO:10 | Chimera 1 |

TABLE III-continued

| Number | Sequence 5'→3' (including enzyme site)* | | Construct |
|---|---|---|---|
| 3742 | AACATTTCTTGGGATGAAGTATCATATGACAAAGAAGGTAAC GAAATTGTTCAA | SEQ ID NO:11 | Chimera 2 |
| 3743 | TTGAACAATTTCGTTACCTTCTTTGTCATATGATACTTCATC C CAAGAAATGTT | SEQ ID NO:12 | Chimera 2 |
| 3744 | TATGATCCTGAAGGTAACGAAGTATTAACTCATAAAAACTGG AGCGAAAAC | SEQ ID NO:13 | Chimera 3 |
| 3745 | GTTTTCGCTCCAGTTTTTATGAGTTAATACTTCGTTACCTTC A GGATCATA | SEQ ID NO:14 | Chimera 3 |
| 3746 | AACGAAATTGTTCAACATAAAACATGGGATGGAAACAATAAA AGCAAGCTAGCT | SEQ ID NO:15 | Chimera 4 |
| 3747 | AGCTAGCTTGCTTTTATTGTTTCCATCCCATGTTTTATGTTG A ACAATTTCGTT | SEQ ID NO:16 | Chimera 4 |
| 3748 | CATAAAAACTGGAGCGAAAACTATCAAGATAAAACAGCTCAT TTCACATCGTCCATC | SEQ ID NO:17 | Chimera 5 |
| 3749 | GATGGACGATGTGAAATGAGCTGTTTTATCTTGATAGTTTTC GCTCCAGTTTTTATG | SEQ ID NO:18 | Chimera 5 |
| 3750 | AATAAAAGCAAGCTAGCTCATTATTCAACAGTAATCTATTTG CCTGGTAACGCG | SEQ ID NO:19 | Chimera 6 |
| 3751 | CGCGTTACCAGGCAAATAGATTACTGTTGAATAATGAGCTAG CTTGCTTTTATT | SEQ ID NO:20 | Chimera 6 |
| 3752 | GCTCATTTCACATCGTCCATCCCTCTTGAAGCTAACGCGAGA AATATTAATGTT | SEQ ID NO:21 | Chimera 7 |
| 3753 | AACATTAATATTTCTCGCGTTAGCTTCAACAGGGATGGACGA TGTGAAATGAGC | SEQ ID NO:22 | Chimera 7 |
| 3754 | CCTGGTAACGCCAGAAATATTAGAATAAAAGCAAGAGAATGC ACTGGTTTAGCTTGG | SEQ ID NO:23 | Chimera 8 |
| 3755 | CCAAGCTAAACCAGTGCATTCTCTTGCTTTTATTCTAATATT T CTCGCGTTACCAGG | SEQ ID NO:24 | Chimera 8 |
| 3756 | TGGGAATGGTGGAGAGATGTAATTGATGACCGG | SEQ ID NO:25 | Chimera 9 |
| 3757 | CCGGTCATCAATTACATCTCTCCACCATTCCCA | SEQ ID NO:26 | Chimera 9 |
| 3758 | GGGAATGGTGGAGAACGGTAATTAGTGAATATGATGTTCCAC TTGTGAAAAATAGAAAT | SEQ ID NO:27 | Chimera 10 |
| 3759 | ATTTCTATTTTTCACAAGTGGAACATCATATTCACTAATTAC C GTTCTCCACCATTCCC | SEQ ID NO:28 | Chimera 10 |
| 3760 | GACCGGAACTTACCACTTACAAATAATATAAATATCTCCATC TGGGGC | SEQ ID NO:29 | Chimera 11 |
| 3761 | GCCCCAGATGGAGATATTTATATTATTTGTAAGTGGTAAGTT CCGGTC | SEQ ID NO:30 | Chimera 11 |
| 3580 | AGATCCAGGGTATAAAGTGGTGCCCCAGATGGAGAT | SEQ ID NO:31 | Chimera 12 |
| 3581 | ATCTCCATCTGGGGCACCACTTTATACCCTGGATCT | SEQ ID NO:32 | Chimera 12 |
| 3799 | GAAAACAATAAAAGCAAGACAGCTCATTTCACATCGTCC | SEQ ID NO:33 | His-L461T and DP-L4017 |
| 3800 | GGACGATGTGAAATGAGCTGTCTTGCTTTTATTGTTTTC | SEQ ID NO:34 | His-L461T and DP-L4017 |
| 3931 | TTTCTGCAGAGAAACACGCGGATGAAATCGATA (Pst1) | SEQ ID NO:35 | DP-L4017 |
| 3932 | AAAAGAGCTCTCTGGAATTGAGGATGATTTCTTT (Sac1) | SEQ ID NO:36 | DP-L4017 |

2. Construction of the PFO Expression Vector

Mature PFO was amplified by PCR from p1868 (Jones, S., and D. A. Portnoy. 1194b. Intracellular growth of bacteria. *Methods Enzymol.* 236:463-467), a plasmid carrying the coding sequence for mature PFO from *Clostridium perfringens*, using the primers, templates, and restriction sites. This fragment was ligated into pET28a (Novagen) and later expressed with BL21(DE3)PlysS, strain DP-4167.

3. Construction of the Domain Chimeras, Subdomain Chimeras, and Single Amino Acid Mutation Expression Vectors The fourth domain of LLO was replaced by PFO domain 4 using splicing by overlap extension PCR (Horton, R. M., Z. L. Cai, S. N. Ho, and L. R. Pease. 1990. Gene splicing by overlap extension: tailor-made genes using the polymerase chain reaction. *Biotechniques.* 8:528-535.). The subdomain chimeras and the single amino acid mutations indicated in were constructed by modifying p3570 with the protocol published in the Quickchange™ site-directed mutagenesis kit (Stratagene) and the primers listed in Table III.

4. Hemolytic Activity Screening of Recombinant Proteins

*E. coli* expression strains were grown overnight in LB containing 30 µg/ml kanamycin (LB—KAN). 400 µl of the overnight culture was added to 10 ml LB—KAN and grown for 1.5 h, and then 1 mM IPTG was added. This culture was incubated at 30° C., shaking for 3 h. Cultures were pelleted and then resuspended in 1 ml storage buffer (140 mM sodium chloride, 4 mM potassium chloride, 10 mM sodium phosphate, 0.5 mM DTT, pH 6.0) with 1 mM PMSF. The samples were sonicated on ice and cleared by centrifugation.

The quantitative assay was performed in a 96-well V-bottom styrene plate (Corning Inc.) with either neutral hemolysis buffer (35 mM sodium phosphate, 125 mM sodium chloride, 0.5 mg/ml BSA, pH 7.4, using acetic acid) or acidic hemolysis buffer (same as neutral hemolysis buffer but pH 5.5). Samples were serially diluted, and then 0.5% sheep red blood cells (HemoStat Laboratories) were added to each well. The plate was incubated, shaking at 37° C., and then pelleted in the V-bottom. Supernatant was transferred from the V-bottom plate into equivalent locations in a flexible polyvinyl chloride flat bottom 96-well plate (Becton Dickinson), and the absorbance at 450 nm for each well was measured (Spectramax340) and analyzed with SoftMax Pro v1.2 software (Molecular Devices Corp.). Hemolytic units were defined as the dilution of the sample at which 50% of the sheep red blood cells had been lysed.

5. Overexpression and Purification of 6× his-Tagged LLO Proteins and 6× his-Tagged PFO from *E. coli*

Recombinant strains were grown, shaking at 37° C., in LB—KAN to stationary phase. 20 ml of this culture was inoculated into 1 liter of LB—KAN and incubated, shaking at 30° C., for 90 min. Expression was induced by the addition of 1 mM IPTG, and the culture was incubated, shaking at 30° C., for 6 h. The bacterial pellet was harvested by centrifugation, resuspended in 40 ml cold lysis buffer (50 mM sodium phosphate, pH 8.0, 1 M sodium chloride, 20 mM imidazole, 10 mM 2-mercaptoethanol, 1 mM PMSF), and lysed in a French pressure cell at 12,000 psi. The lysate was centrifuged for 20 min at 17,000 g. The supernatant was collected and mixed into 5 ml Ni—NTA resin (QIAGEN) equilibrated in lysis buffer. The slurry was stirred at 4° C. for 60 min to bind his-tagged protein to the resin. To remove unbound protein, the resin was packed into a column and washed with lysis buffer by dropwise gravity flow until UV absorbance of the eluate reached baseline, and then it was washed with wash buffer (lysis buffer, pH 6.0, 10% glycerol, 0.1% Tween 20). Washed resin was removed from the column, resuspended in elution buffer (lysis buffer, pH 6.0, and 800 mM imidazole), and incubated 10 min on ice, after which the supernatant was collected. This procedure was performed twice, yielding 6 ml eluate. Eluate was dialyzed in cassettes (Pierce Chemical Co.) within autoclaved storage buffer (lysis buffer, pH 6.0, with 1 mM EDTA). Both the Bradford method and UV280 absorbance determined protein concentrations. The procedure yielded ~25 mg protein per liter starting culture. Aliquots not used immediately were stored in storage buffer with 50% glycerol at −80° C.

6. Allelic Exchange of LLO L461T

To introduce the LLO L461T mutation onto the 10403S chromosome, a DNA fragment was produced with the method of splicing by overlap extension PCR, using the primers, templates, and restriction enzymes in Table 1, and then ligated into the temperature-sensitive plasmid vector pKSV7. Allelic exchange was performed as described previously (Camilli, A., L. G. Tilney, and D. A. Portnoy. 1993. Dual roles of plcA in *Listeria monocytogenes* pathogenesis. *Mol. Microbiol.* 8:143-157.). Strains were verified initially by detecting the loss of an Nhe1 site in a chromosomal PCR product containing the mutation.

7. Animal Studies $LD_{50}$ by intravenous infection was established as previously described using BALB/c mice (Portnoy, D. A., P. S. Jacks, and D. J. Hinrichs. 1988. Role of hemolysin for the intracellular growth of *Listeria monocytogenes*. *J. Exp. Med.* 167:1459-1471.).

8. Phagosomal Escape Assay

The percentage of bacteria that had escaped from the phagosome was determined by evaluating the presence of F-actin-coated bacteria within the macrophage, similar to an experiment previously described (Jones, S., and D. A. Portnoy. 1994a. Characterization of *Listeria monocytogenes* pathogenesis in a strain expressing perfringolysin O in place of listeriolysin O. *Infect. Immun.* 62:5608-5613). C57/BL6 BMØs in DME, 10% FBS, with or without 0.5 µM bafilomycin A1 (Calbiochem), on a coverslip were infected for 15 min, resulting in a bacterium within 10% of the cultured macrophages. Macrophages were washed with Ringer's buffer (5 mM NaCl, 5 mM KCl, 2 mM $CaCl_2$, 1 mM $MgCl_2$, 2 mM $NaH_2PO_4$, 10 mM Hepes, 10 mM glucose, pH 7.2) and 25 µg/ml gentamicin was added. At 120 min after infection, the macrophages were fixed for 15 min with cytoskeletal fixative (40 mM Hepes, 10 mM EGTA, 0.5 mM EDTA, 5 mM $MgSO_4$, 33 mM potassium acetate, 0.02% sodium azide, 5% polyethylene glycol 400, 4% paraformaldehyde), washed, permeabilized with PBS, containing 2% goat serum and 0.3% Triton X-100, and stained with Texas red-phalloidin (Molecular Probes) and DAPI (Molecular Probes). A total of 50 macrophages harboring bacteria were examined for each bacterial strain in each of four experiments.

The determination of phagosomal pH was performed essentially as previously described (Beauregard, K. E., K. D. Lee, R. J. Collier, and J. A. Swanson. 1997. pH-dependent perforation of macrophage phagosomes by listeriolysin O from *Listeria monocytogenes*. *J. Exp. Med.* 186:1159-1163.) with the following modifications. In brief, fluid-phase fluorescein dextran, molecular weight 10,000 (Molecular Probes), was added to the bacteria-containing media used to infect macrophages. Phagosomes containing both 10-kD fluorescein dextran and bacteria were photographed every 30 s with a Quantix cooled charge-couple device camera (Photometrics) through fluorescent microscopy using a Nikon TE300 inverted microscope (Nikon), with phase-contrast and excitation wavelengths 485 and 440 nm and emission measurement at 520 nm. Images and the 485:440 ratio were collected until perforation was indicated by loss of dye from the vacuole. The 485:440 ratio measured just before perforation was compared with a standard curve to establish pH, as described in the published methods.

9. Cytotoxicity Assays—Growth in J774 Macrophage-Like Cells

Intracellular growth of *L. monocytogenes* was performed as previously described (Jones and Portnoy, Intracellular growth of bacteria. (1994b) *Methods Enzymol.* 236:463-467).

10. Flow Cytometry

Flow cytometry was performed on cultures of BMØs from CD-1 mice as previously described (Portnoy, D. A., P. S. Jacks, and D. J. Hinrichs. 1988. Role of hemolysin for the intracellular growth of *Listeria monocytogenes*. J. Exp. Med. 167:1459-1471.). BMØ were chosen for this assay because infected J774 are difficult to remove from tissue culture dishes without causing plasma membrane damage, whereas BMØ lift from the dish when incubated at 4° C. $10^6$ macrophages were plated on 60-mm Lab-tek nontissue culture dishes (Fisher Scientific) overnight in bone marrow macrophage media (DME, 20% heat-deactivated FBS, 30% L cell supernatant containing CSF-1 in DME, 2 mM glutamine, 1 mM pyruvate, 0.1% 2-mercaptoethanol). Monolayers were infected with $10^7$ washed bacteria for 30 min resulting in at least one bacterium per cell. 60 min after infection, 50 µg/ml gentamicin was added. 3 h after infection, the cell monolayer was washed to remove the gentamicin, and then fresh medium was added to the dish. 7 h after infection, medium from each culture was collected. 4° C. PBS was then added and the dish was stored at 4° C. for ~30 min. Release of macrophages from the dish was monitored by microscopy. The macrophage-containing PBS was added to the previously removed media and centrifuged at 4° C. The pellet was washed with 4° C. PBS, 10% FBS. Cell pellets were resuspended in PBS (10% FBS) and passed through a 70-µm cell strainer (Becton Dickinson). 1 µg propidium iodide (Molecular Probes) was added to each sample. Samples were analyzed with a flow cytometer (EPICS XL-MCL; Beckman Coulter).

11. LDH Release Assay

LDH release assays were performed using the Cytotox 96® nonradioactive cytotoxicity assay (Promega), according to manufacturer's instructions and methods described previously (Decatur, A. L., and D. A. Portnoy. 2000. A PEST-like sequence in listeriolysin O essential for *Listeria monocytogenes* pathogenicity. Science. 290:992-995) with $2\times10^4$ J774 cells per well infected to achieve at least one bacterium per cell. Neutralizing anti-LLO monoclonal antibodies were supplied by Brian Edelson and Emil Unanue (Washington University School of Medicine, St. Louis, Mo.).

12. Intracellular LLO Analysis

Intracellular levels of LLO were studied with previously established methods (Moors, M. A., B. Levitt, P. Youngman, and D. A. Portnoy. 1999. Expression of listeriolysin O and ActA by intracellular and extracellular *Listeria monocytogenes*. Infect. Immun. 67:131-139.) and the following modifications. In brief, J774 cells were infected with *L. monocytogenes* strains for 30 min and then washed, and 50 µg/ml gentamicin was added at 60 min. 4 h after infection, methionine-starved cells were pulsed with [$^{35}$S]methionine (NEN Life Science Products) for 1 h. At 5 h, macrophages were lysed, LLO was immunoprecipitated, and one half of the sample was subjected to SDS-PAGE for autoradiography and the other half run for analysis on a Phosphorimager 445 SI (Molecular Dynamics) and analyzed using Imagequant software (Molecular Dynamics). Monoclonal anti-LLO antibodies were supplied by Pascale Cossart (Institute Pasteur, Paris, France). The relative number of bacteria in each assay was established by lysing the infected J774 on coverslips in dishes processed in tandem with the radiolabeled dishes. Lysate was subsequently plated on LB-agar plates to determine colony-forming units.

13. Plaque Assay

Plaquing assays within L2 cell monolayers were performed as described previously (Sun, A., A. Camilli, and D. A. Portnoy. 1990. Isolation of *Listeria monocytogenes* small-plaque mutants defective for intracellular growth and cell-to-cell spread. Infect Immun. 58:3770-3778.), with modifications to the methods of measurement (Skoble, J., D. A. Portnoy, and M. D. Welch. 2000. Three regions within ActA promote Arp2/3 complex-mediated actin nucleation and *Listeria monocytogenes* motility. J. Cell Biol. 150:527-538.). In brief, L2 cells were grown to confluency in six-well tissue culture dishes and then infected with bacteria for 1 h. Subsequently, DME-agar containing gentamicin was added and plaques were grown for 3 d. Living cells were visualized by adding on day 3 an additional DME-agar overlay containing neutral red (GIBCO BRL) and incubating overnight.

B. Results

1. Identification of Amino Acid Residues Within LLO that Confer an Acidic pH Optimum We sought to isolate a mutation in LLO that increased its activity at a neutral pH and thus caused LLO to act like PFO. We began with the assumption that PFO contains a sequence that facilitates its activity over a broad pH range, and placing this sequence in LLO would alter LLO's pH profile. Because domain 4 of PFO was implicated in membrane binding and insertion, it was deemed a good candidate for regulating pH-dependent cytolysis. A chimeric protein consisting of the first three domains of LLO and the fourth domain of PFO was generated. The domain 4 chimera, LLO, and PFO were expressed as COOH-terminally his-tagged recombinant proteins in *Escherichia coli* and purified for analysis of hemolytic activity. The domain 4 chimera was less active than either PFO or LLO, yet its activity at both pH 5.5 and 7.4 was similar. We interpreted these results to indicate that within the fourth domain of LLO were sequences that control the pH activity profile.

Next, we divided the fourth domain of LLO into 12 sub-domains, each containing amino acids dissimilar to those of PFO, and swapped those regions of dissimilarity from PFO into LLO. Two chimeras (5 and 10) showed a dramatic reduction in the ratio of activity at an acidic pH to that at a neutral pH. However, chimera 10 was ~10-fold less active than LLO and was not studied further. The four amino acid changes in chimera 5 were then individually introduced into LLO. A single amino acid change, L461T, increased the hemolytic activity of LLO nearly 10-fold at a neutral pH without decreasing specific activity at pH 5.5. Thus, a single amino acid substitution is sufficient to confer the pH activity profile of PFO onto LLO. Additionally, L461T is unique to the CDC of the pathogenic species of the *Listeria* genus.

2. The L461T Mutation in LLO Reduces Virulence

Having established that the L461T mutation conferred greater activity on purified LLO at a neutral pH, we introduced the mutation onto the chromosome of *L. monocytogenes* by allelic exchange. The resulting strain, DP-L4017, was used for further studies. The mutation had no effect on bacterial growth in vitro. Supernatant fluid derived from cultures of LLO L461T bacteria had a quantity of LLO similar to the wild type and had hemolytic activities at pH 5.5 and 7.4 similar to those of the purified proteins from *E. coli.*

The capacity of the LLO L461T mutant to grow in animals was evaluated by the lethal dose-50 ($LD_{50}$) in the mouse listeriosis model. In BALB/c mice, the $LD_{50}$ of the LLO L461T mutant was >3×10$^6$ as compared with an $LD_{50}$ of 1-3×10$^4$ for wild-type bacteria. These data indicate that LLO pH dependence contributes to the in vivo growth of *L. monocytogenes*.

3. The LLO L461 T Mutation Does Not Affect the Efficiency or pH of Phagosomal Escape Based on the observation that LLO has an acidic pH optimum and the bacteria escape from phagosomes at an acidic pH (Beauregard et al., Exp. Med. (1997) 186:1159-1163.), we hypothesized that a mutant LLO with greater activity at a neutral pH may act prematurely and not mediate escape efficiently. We used a fluorescence-based assay to monitor escape from the phagosome based on the observation that bacteria within the cytosol nucleate host actin filaments on their surface, whereas bacteria in vacuoles do not. We found that the LLO L461T mutant escaped from the phagosome of bone marrow-derived macrophages (BMØ) similarly to wild-type bacteria, 72±2% versus 76±2%, respectively, after 2 h.

Previous studies have indicated that preventing acidification of the phagosome with the vacuolar proton ATPase inhibitor bafilomycin A1 limits *L. monocytogenes* escape to the cytosol. We reasoned that escape of the LLO L461T mutant might not be affected by bafilomycin A1 treatment because its cytolysin was active at a neutral pH. However, when bafilomycin A1 was added to the macrophages, both the mutant and the wild-type bacteria escaped less efficiently. When bafilomycin A1 was present throughout the assay, both strains escaped with about a third of the efficiency of untreated controls.

Because treatment with bafilomycin A1 prevented escape of the LLO L461T mutant as well as the wild-type bacteria, it would appear that the additional activity of the mutant at a neutral pH does not eliminate the requirement for phagosome acidification. Therefore, we measured the pH of bacterium-containing phagosomes using a pH-sensitive fluid-phase fluorescent dye to determine if the LLO L461T mutant altered the phagosomal maturation process. We found that phagosomes containing the LLO L461T mutant reached an average minimum pH of 5.5±0.3 before perforation, similar to that of the wild type, which reached a minimum mean pH of 5.7±0.2. We concluded that the LLO L461T mutation had no effect on phagosomal acidification or escape, and that phagosomal acidification was necessary for the escape of the LLO L461T mutant as well as for wild type. Therefore, it is unlikely that the LLO L461T mutant's virulence defect reflects a reduced ability to escape from phagosomes or an effect on phagosome maturation. The defect is likely due to the alteration of a different part of the pathogenic life cycle.

4. *L. monocytogenes* LLO L461T damages host cell membranes Because the LLO L461T mutant had no defect in phagosomal escape, we next examined the capacity of the bacteria to grow in host cells using a quantitative tissue culture assay (Portnoy et al., 1988, supra). In this assay, adding the antibiotic gentamicin to the culture medium kills extracellular bacteria but has no measurable effect on the growth of intracellular wild-type bacteria. Between 2 and 5 h after infection, the LLO L461T mutant grew well within J774 macrophages with an average apparent doubling time of 58±8 min, slightly longer than the wild-type doubling time of 42±4 min. Strikingly, between 5 and 8 h after infection, the LLO L461T mutant grew with a nearly twofold longer average apparent doubling time (159±30 min compared with the wild-type doubling time of 83±8 min). Additionally, the LLO L461T mutant did not grow to as high a maximum number of bacteria.

We reasoned that the LLO L461T mutant's longer apparent doubling times and lower maximum bacterial numbers could reflect either a decrease in the overall growth rate or, more likely, an increase in the death of a subpopulation of intracellular bacteria. The analysis is complicated by the fact that after 5 h, *L. monocytogenes* spread from cell to cell. To eliminate cell-to-cell spread from the analysis, an in-frame deletion was introduced within the actA gene. The resulting strain was fully capable of vacuolar escape and intracellular growth within the original host cell, but was unable to nucleate actin filaments and thus unable to enter the secondary cell's double-membraned vesicle or spread from cell to cell. As previously observed, a ΔActA strain expressing wild-type LLO grew intracellularly for the first 8 h, after which bacterial numbers rapidly dropped due to death of the host cell and influx of gentamicin. A corresponding drop in the number of LLO L461T ΔActA bacteria was observed, but the drop occurred at 5 h instead of at 8 h observed for the wild type. Treatment with the pharmacological inhibitor of actin polymerization, cytochalasin D, which prevents bacterial intracellular motility, led to similar growth defects as the deletion of ActA (unpublished data). Thus, the growth defect of LLO L461T bacteria was more pronounced when cell-to-cell spread was inhibited. (As shown in the next section, the LLO L461T mutant is not defective in the ability to spread from cell to cell.) For both wild-type and LLO L461T bacteria, the drop in colony-forming units was only observed when gentamicin was present in the assay medium. When host membranes become permeabilized during a cell culture infection, gentamicin present in the culture medium enters the host cell and kills intracellular bacteria. Therefore, the gentamicin-dependent drop in numbers of intracellular bacteria suggested that host membranes had been permeabilized. Because the LLO L461T ΔActA mutant died earlier than the wild-type LLO ΔActA strain, and because this occurred in a gentamicin-dependent manner, we hypothesized that the greater activity of LLO L461 Tat a neutral pH led to earlier permeabilization of the host cell membrane. If this hypothesis were true, damage could be monitored by detecting release of the host cell enzyme lactate dehydrogenase (LDH) from the cytosol of the J774 cells into the culture medium. During a 7 h infection with wild-type bacteria, very little LDH was released either in the presence or absence of gentamicin. In the absence of gentamicin, both the LLO L461T- and LLO L461T ΔActA-infected cells released nearly 100% of their LDH, indicating a major disruption of the host plasma membrane. Interestingly, when J774 cells were incubated in the constant presence of gentamicin, very little LDH was released during infection by any strain. Presumably, permeabilization of the cell allowed the influx of gentamicin, which then killed the intracellular bacteria and prevented further permeabilization and LDH release. When gentamicin was removed after 2 h, only the J774 cells infected with the LLO L461T ΔActA mutant released high quantities of LDH. When a monoclonal antibody that neutralizes LLO activity was added extracellularly to the J774 cells, there was no effect on LDH release, indicating that toxicity is mediated by intracellular LLO (unpublished data).

A more sensitive method to test the integrity of the plasma membrane uses the membrane-impermeant dye propidium iodide. When membrane integrity is compromised, the dye enters the cell and increases its fluorescence upon binding cellular DNA. Staining can be measured by flow cytometry. After infection with the wild-type bacteria, most macrophage host cells still excluded the dye. In contrast, infection with the LLO L461T mutant led to permeabilization of about half of the macrophages, and infection with the LLO L461T ΔActA mutant permeabilized most of the macrophages.

To address the possibility that the LLO L461T molecule had altered cytosolic stability, which could lead to increased cytotoxicity, we infected J774 cells and examined the steady-state quantity of cytosolic LLO. We found that there was approximately twofold more cytosolic LLO L461T than wild type. However, when J774 cells were infected with a strain harboring two copies of the gene encoding LLO, so that they produce twice as many hemolytic units, a similar quantity of LLO to the LLO L461T mutant was observed. However, despite the fact that infection with the merodiploid led to a concentration of LLO in the cytosol similar to the mutant, the merodiploid damaged the host cell's plasma membrane no more than the wild-type bacteria. Together, these data suggested that the decreased growth of the LLO L461T mutant was associated with permeabilization of the host cells due to increased activity of the LLO L461T at a neutral pH, and was not due to an increased cytosolic concentration of LLO.

5. *L. monocytogenes* Strain LLO L461T is Not Defective in Cell-To-Cell Spread

LLO plays an essential role in the escape of *L. monocytogenes* from both the primary phagosome and the secondary double membrane-bound vesicle formed during cell-to-cell spread. The results described above did not directly address whether the LLO L461T mutation affects bacterial cell-to-cell spread. We examined the ability of bacteria to spread from cell to cell by measuring the diameter of plaques formed in L2 monolayers after 3 d in the presence of different concentrations of gentamicin. Plaque diameter is a measure of a bacterium's ability to grow, move through the host cell cytosol, enter an adjacent cell, and escape from the secondary vesicle formed in the adjacent cell. At low gentamicin concentrations, the LLO L461 T strain's plaque was equal in diameter to the wild type, whereas at high concentrations the mutant had a severe plaquing defect. Thus, the capacity of an LLO L461T mutant to form plaques was gentamicin dependent.

Two *L. monocytogenes* mutants with slight defects in either actin-based motility or escape from the double-membraned vesicle were analyzed as controls. The corresponding reduction in the size of plaques formed by these mutants was independent of gentamicin concentration. Also, the merodiploid strain with two copies of LLO formed plaques identical to wild type at each gentamicin concentration. Therefore, we concluded that LLO L461T was fully capable of mediating cell-to-cell spread and escape from the double-membraned vesicle. Additionally, based on the data observed, we concluded that the plaque defect seen at high gentamicin concentrations reflected bacteriocidal activity of the antibiotic on intracellular bacteria that entered cells subsequent to LLO-mediated damage to the host cell membrane. Conversely, low concentrations of gentamicin did not allow the influx of sufficient quantities of the antibiotic to negatively affect the bacteria. These conclusions agree with the results observed for the merodiploid, which did not permeabilize host membranes to propidium iodide nor form gentamicin-sensitive plaques.

C. Conclusion

The DP-L4017 strain expresses an LLO mutant which is 10-fold more hemolytic at neutral pH, relative to wild type LLO, which results in quicker damage to the host cell. This strain was also found to be 100-fold less virulent, by LD50 in BALB/c mice, and by 48 hours was 74 and 21-fold less abundant in the spleen and liver, respectively, than wild type bacteria, in a competitive index assay. As such, the strain exhibits increased cytotoxity and decreased virulence as compared to wild type. The strain establishes an active infection in the mouse model that is limited by its cytotoxicity and cleared efficiently from the host system.

The above attributes make this strain an acceptable attenuated *Listeria* strain for use in a variety of applications, as described above.

II. DP-L4057

The DP-L4057 strain contains the mutation S44A in LLO (serine to alanine amino acid change in LLO at amino acid position 44) and was constructed using protocols analogous to those described above. The S44A mutation was constructed to interrupt a potential mitogen-activated protein kinase (MAPK) phosphorylation site with the PEST-like sequence at the N-termini of LLO, which has been implicated in protein degradation within the cytosol of mammalian cells. After 48 hours strain DP-L4057 is 580 and 740-fold less abundant than wild type bacteria in the spleen and liver, respectively, using a competitive index assay, as described previously (Auerbuch, V., L. L. Lenz, and D. A. Portnoy 2001 Development of a competitive index assay to evaluate the virulence of *Listeria monocytogenes* acta mutants during primary and secondary infection of mice. *Infect. Immun.* 69: 5953-5957). As such, the strain exhibits increased cytotoxity and decreased virulence as compared to wild type. The strain establishes an active infection in the mouse model that is limited by its cytotoxicity and cleared efficiently from the host system.

The above attributes make this strain an acceptable attenuated *Listeria* strain for use in a variety of applications, as described above.

III. DP-L4384

The DP-L4384 strain contains both of the above described mutations, i.e., mutation S44A and mutation L461T) in LLO and was constructed using protocols analogous to those described above. The strain incorporates all of the properties of the above two described strains. After 48 hours strain DP-L4384 is $4.6 \times 10^5$ and $1.7 \times 10^5$-fold less abundant than wild type bacteria in the spleen and liver, respectively, in a competitive index assay (Auerbuch, V. et al, supra). As such, the strain exhibits increased cytotoxity and decreased virulence as compared to wild type. The strain establishes an active infection in the mouse model that is limited by its cytotoxicity and cleared efficiently from the host system.

The above attributes make this strain an acceptable attenuated *Listeria* strain for use in a variety of applications, as described above.

IV. DP-L4042

The DP-L4042 was constructed as described in Decatur & Portnoy, Science (Nov. 3, 2000) 290: 992-995. This strain contains a deletion of residues 34 to 59 of LLO, and therefore deletes the entire PEST-like sequence-found at the N-terminus of LLO. The strain is extremely cytotoxic, and therefore is essentially undetectable in the competitive index assay after 48 hours. The strain has an $LD_{50}$ of $2 \times 10^8$, approximately 10,000 times higher than the wild-type bacteria. As such, the strain exhibits increased cytotoxity and decreased virulence as compared to wild type. The strain establishes an active infection in the mouse model that is limited by its cytotoxicity and cleared efficiently from the host system.

The above attributes make this strain an acceptable attenuated *Listeria* strain for use in a variety of applications, as described above.

V. Additional Characterization of LLO Mutant Strains

A. Materials and Methods

1. Strains, Growth Conditions, and Reagents

The wild-type *L. monocytogenes* strain used for these studies was 10403S (Portnoy, D. A., T. Chakraborty, W. Goebel, and P. Cossart. 1992. Molecular determinants of *Listeria monocytogenes* pathogenesis. *Infect Immun* 60:1263-1267). *L. monocytogenes* strains with deletions of actA were constructed by allelic exchange as described previously (Camilli, A., L. G. Tilney, and D. A. Portnoy. 1993. Dual roles of plcA in *Listeria monocytogenes* pathogenesis. *Mol Microbiol* 8:143-157; Skoble, J., D. A. Portnoy, and M. D. Welch. 2000. Three regions within ActA promote Arp2/3 complex-mediated actin nucleation and *Listeria monocytogenes* motility. *J Cell Biol* 150:527-538). Strain LLO L461T (DP-L4017) was described previously (Glomski, I. J., M. M. Gedde, A. W. Tsang, J. A. Swanson, and D. A. Portnoy. 2002. The *Listeria monocytogenes* hemolysin has an acidic pH optimum to compartmentalize activity and prevent damage to infected host cells. *J Cell Biol* 156:1029-1038). A summary of the strains used in this study can be found in Table II. Bacteria were grown in 3 ml brain heart infusion broth (BHI; Becton Dickinson, Sparks, Md.) slanted without agitation in 15 ml conical tubes at 30° C. overnight, unless otherwise noted.

Tissue culture cells were grown in DMEM (Gibco-BRL) 7.5% heat deactivated fetal bovine serum (FBS)(Hy-Clone, Logan, Utah) 2 mM glutamine (DMEM; Gibco-BRL) at 37° C. and 5% $CO_2$, unless otherwise noted. All chemicals were purchased from Sigma-Aldrich, St. Louis, Mo., unless otherwise noted. 6 to 8 week old Female C57BL/6 (Jackson Labs, Bar Harbor, Me.) mice were used for infection and bone marrow isolation, unless otherwise noted, under the University of California, Berkeley animal use protocol #R235-0701B. RB6-8C5 monoclonal antibodies were produced (Strategic BioSolutions Newark, Del.) from a hybridoma generously donated by Robert North and Ronald LaCourse of the Trudeau Institute. The ascites was harvested from nude mice, and then partially purified by precipitation with 45% ammonium sulfate using endotoxin-free conditions. The antibody was subsequently resuspended and dialyzed in PBS.

2. Construction of LLO Mutants

Strain LLO S44A (DP-L4057) was produced using splicing by overlap extension PCR (Horton, R. M., Z. L. Cai, S. N. Ho, and L. R. Pease. 1990. Gene splicing by overlap extension: tailor-made genes using the polymerase chain reaction. *Biotechniques* 8:528-535) to change serine 44 to alanine using the following oligo nucleotides (Operon Technologies): DP-1569 GGGTCGACTCCTTTGATTAGTATATTCCT (SalI) (SEQ ID NO:37), DP-1700 TTTGGATAAGCTTGAGCATATT (Hind3) (SEQ ID NO:38), DP-3820 GCACCACCAGCAGCTCCGCCTGCMG(SEQ ID NO:39) and DP-3821 CTTGCAGGCGGAGCTGCTGGTGGTGC (SEQ ID NO:40). DP-1569 was paired with DP-3821, and DP-3820 with DP-1700 to produce 382 and 480 bp. DNA fragments, respectively, using pfu polymerase (Stratagene), and genomic DNA from 10403S as a template. The two fragments were then spliced to form a 862 bp fragment that was cut with SalI and Hind3 and ligated into a similarly cut pKSV7 plasmid for allelic exchange (Camilli,et al., supra). The *L. monocytogenes* strains were initially screened with AluI digestion, which was introduced by the S44A mutation, then subsequently sequenced to verify the mutation. Strain LLO S44A L461T (DP-L4384) was produced by introducing the plasmid used to produce LLO L461T (p4005) into DP-L4057 for allelic exchange (Glomski et al., supra). Clones were screened for the loss of an NheI site, introduced by the L461T mutation, and then subsequently verified by sequencing.

All of the mutant LLO strains were marked for the competitive index assay by transducing the gene for erythromycin resistance from strain DP-L3903 using ØU153, as described by Hodgson (Auerbuch, V., L. Lenz, and D. Portnoy. 2001. Development of a competitive index assay to evaluate the virulence of *Listeria monocytogenes* actA mutants during primary and secondary infection of mice. *Infection and Immunity*; Hodgson, D. A. 2000. Generalized transduction of serotype ½ and serotype 4b strains of *Listeria monocytogenes*. *Mol Microbiol* 35:312-323). Briefly, phage U153 isolated from DP-L3903 were added to the recipient strain while in mid-log growth, 10 mM $CaCl_2$ and 10 mM $MgCl_2$ were added, and bacteria were incubated at room temperature for 1 hour, with occasional mixing. After one hour, 0.1 μg/ml erythromycin was added for 30 minutes, and then the mixture was spread on 1 μg/ml erythromycin BHI-agar plates and incubated at 37° for 2 days. Transduction of the erythromycin resistance gene was verified by PCR analysis using the primers DP-4409 CCCMGCTTCTAAAGTTATGGAAATAAGAC (SEQ ID NO:41) and DP-4410 CCGAGCTCACGGATTTTGGTACTTGAT (SEQ ID NO:42) that flank erm in Tn917-LTV3. Additionally, the newly isolated resistant strain was competed against the parental non-resistant strain in the mouse to confirm that there was no alteration in virulence. The resulting strains were named as follows: LLO L461T Erm (DP-L4157), LLO S44A Erm (DP-L4382), and LLO S44A L461T Erm (DP-L4385).

3. Phagosomal Escape Assay

The percentage of bacteria that had escaped from the phagosome was determined by indirect immunofluorescence as described previously (Jones, S., and D. A. Portnoy. 1994. Characterization of *Listeria monocytogenes* pathogenesis in a strain expressing perfringolysin O in place of listeriolysin O. *Infect Immun* 62:5608-5613). Briefly, bone-marrow derived macrophages (described below) on a coverslip were infected for 30 minutes, washed with PBS, and then 10 μg/ml gentamicin was added at 60 minutes. At 90 minutes, the macrophages were fixed with 4% formalin-PBS. Before permeabilization, extracellular bacteria were bound with Bacto-*Listeria* O rabbit serum (Difco Laboratories), and visualized with AMCA-conjugated donkey anti-rabbit secondary antibodies (Jackson Immunoresearch Labs, West Grove, Pa.). Subsequently, the macrophages were permeabilized with Triton-X100, and stained with rhodamine phalloidin and Bacto-*Listeria* O rabbit serum. Bacto-*Listeria* O serum bound to intracellular bacteria, which is not bound by AMCA antibodies, was visualized with FITC goat anti rabbit IgG serum. A minimum of 200 bacteria-associated macrophages from nine different coverslips were examined for each bacterial strain.

4. Plaque Assay

Plaquing assays within L2 cell monolayers were performed as described previously (Jones, S., and D. A. Portnoy. 1994, supra), with modifications to the methods of measurement (Skobel et al., supra). Briefly, L2 cells were grown to confluency in 6-well tissue culture dishes, and then infected with bacteria for 1 hour. Subsequently, DMEM agar containing 5 μg/ml gentamicin was added and plaques were grown for 3 days. Living cells were visualized by adding on day 3 an additional DMEM-agar overlay containing neutral red (Gibco-BRL) and incubating overnight.

5. Cytotoxicity Assays i) Growth in J774 Macrophage-Like Cells

Intracellular growth of *L. monocytogenes* was performed as described previously (Jones, S., and D. A. Portnoy. 1994. Intracellular growth of bacteria. *Methods Enzymol* 236:463-467). Infected J774s were visualized by Dif-Quick® staining (Fisher Scientific, Pittsburg, Pa.) and photographed with a Hamamatsu CCD camera on an inverted NikonTE300 microscope.

ii) Flow Cytometry

Flow cytometry was performed on cultures of bone-marrow-derived macrophages (BMØ) from C57BL/6 mice as previously described (Portnoy, D. A., P. S. Jacks, and D. J. Hinrichs. 1988. Role of hemolysin for the intracellular growth of *Listeria monocytogenes*. *J Exp Med* 167:1459-1471). The assay was performed as previously published (Glomski, et al., supra), with the following modifications. In brief, BMØ monolayers were infected with bacteria for 30 minutes, then washed with PBS, and incubated at 37° until 4 hours post-infection. Unlike the previously published assay, this assay was performed in a shorter time interval and no gentamicin was added because the most cytotoxic strains were adversely affected by the addition of gentamicin even at the earliest time points. The cells were then removed from the dish, stained with propidium iodide, and analyzed by flow cytometry as described.

6. Mouse Infections

Lethal Dose 50 determination was performed by Cerus Pharmaceuticals (Concord, Calif.) by tail vein injection in C57BL/6 mice as previously described (Portnoy et al., 1988, supra). Competitive indexes of LLO mutants, marked with erythromycin resistance, versus wild-type bacteria or single strain infections were performed essentially as previously described (Auerbuch, et al., supra), with the following modifications. Bacterial strains intended for injection into the mouse were grown in BHI until they reached an OD600 of 0.5, then 1 ml samples were frozen at −80° until subsequent use. These frozen samples were thawed and used to inoculate 10 ml of BHI, and grown at 37° until an OD of 0.5. Wild type mice were infected by tail vein injection of $5 \times 10^5$ CFU. RB6-8C5 monoclonal antibody treated were infected with $5 \times 10^3$ CFU, since a dose of $5 \times 10^5$ CFU lead to death before the 48-hour time point. $1 \times 10^7$ CFU were injected in the ΔActA competitive index assay. The mutant bacteria were differentiated from the wild-type bacteria in the competitive index by treating organ lysates with 0.1 pg/ml erythromycin for 30 minutes to induce the resistance gene, then plating the sample on LB-agar plates and 1 μg/ml erythromycin BHI-agar plates to establish a ratio of sensitive (wild type) to resistant (mutant) bacteria at each respective time point. Mice that were treated with RB6-8C5 were injected with 100 μg monoclonal antibody via the tail vein 6 hours before bacterial infection. Gentamicin-treated mice were injected with 1 mg Garamycin® (gentamicin sulfate, Schering Corporation, Kenilworth, N.J.) in PBS subcutaneously six hours prior to organ harvest. 12 hours after injection we found the concentration of gentamicin to be 5.6 μg/ml in the pooled serum of 3 mice (performed by Debra Randall, Stanford University Hospital Clinical Labs, Palo Alto, Calif.), which is sufficient to inhibit bacterial growth.

7. Bacterial Growth in Serum

Mouse blood was removed by cardiac puncture on mice anesthetized with isofluorane (Abbott Labs, Ill.), then allowed to clot overnight at 4°. The clot was removed and the samples were centrifuged to allow separation of serum from any remaining solids. $1 \times 10^3$ bacteria were added to each sample of 50% serum-PBS, and then time points were taken by plating dilutions on LB-agar plates. Incubating the serum at 65° for 30 minutes produced heat-deactivated serum. 8. Tables

TABLE I

*Listeria monocytogenes* strains used in study

| Strain Number | Description |
| --- | --- |
| 10403S | Wild Type |
| DP-L-3903 | Wild Type Erm[ra] |
| DP-L2161 | LLO[b] |
| DP-L4017 | LLO L461T |
| DP-L4057 | LLO S44A |
| DP-L4384 | LLO S44A L461T |
| DP-L4157 | LLO L461T Erm[r] |
| DP-L4382 | LLO S44A Erm[r] |
| DP-L4385 | LLO S44A L461T Erm[r] |
| DP-L3078 | ActA[c] |
| DP-L4038 | ActA LLO L461T |
| DP-L4396 | ActA LLO S44A |
| DP-L4397 | ActA LLO S44A L461T |
| DP-L4403 | ActA LLO L461T Erm[r] |
| DP-L4399 | ActA LLO S44A Erm[r] |
| DP-L4400 | ActA LLO S44A L461T Erm[r] |

[a]Erm[r] indicates erythromycin resistance
[b]LLO indicates that the hly gene has an in-frame deletion in the open reading frame
[c]ActA indicates that the actA gene has an in-frame deletion in the open reading frame

TABLE II

Virulence and Escape Efficiency of Cytotoxic *L. monocytogenes*

| Strain | Lethal Dose-50[a] | Phagosomal Escape (%)[b] | Plaque Size[c] |
| --- | --- | --- | --- |
| WildType | $5 \times 10^4$ | 51 ± 15 | 100% |
| LLOd | $>1 \times 10^9$ | 0 | N.D.[e] |
| LLO L461T | $7.5 \times 10^6$ | 43 ± 9 | 100 ± 2%[f] |
| LLO S44A | $7.5 \times 10^7$ | 63 ± 9 | 14 ± 5% |
| LLO S44A L461T | $>1 \times 10^8$ | 58 ± 8 | N.D. |

[a]Lethal dose 50 is the quantity of bacteria injected into the tail vein that leads to deact of 50% of C57BL/6 mice.
[b]Percent phagosomal escape (±Std. Dev.) is the percentage of actin-coated bacteria versus total bacteria at 90 min. post infection. A minimum of 200 bacteria associated macrophage were counted.
[c]Plaque size, as a percentage of wild-type, in L2 monolayers after 3 days of bacterial growth with 5 μg/ml gentamicin, ±std. dev.
[d]Strain LLO (DP-L2161) was previously published in Jones and Portnoy (1994)
[e]N.D., Plaques not measurable
[f]The plaque size of the LLO L461T strain is sensitive to the gentamicin concentration, as seen in Glomski et al., (2002).

B. Results

1. Construction and Characterization of Cytotoxic Strains in Cell Culture

Four chromosomal alleles of LLO were used in this study (Table 1). Wild-type LLO has an acidic activity optimum and mediates escape from a vacuole with little observed cytotoxicity to the host during subsequent intracellular growth (Glomski, et al., supra; Geoffroy, C., J. L. Gaillard, J. E. Alouf, and P. Berche. 1987. Purification, characterization, and toxicity of the sulfhydryl-activated hemolysin listeriolysin O from *Listeria monocytogenes*. *Infection and Immunity* 55:1641-1646). The previously characterized LLO L461T is active at neutral pH and exhibits some cytotoxicity due to activity in the neutral pH of the host cytosol (Glomski, et al., supra). LLO S44A has an acidic activity optimum, like wild-type LLO, but due to a mutation in the PEST-like sequence has increased levels of LLO in the host cytosol (Decatur, A. L., and D. A. Portnoy. 2000. A PEST-like sequence in listeriolysin O essential for *listeria monocytogenes* pathogenicity [In Process Citation]. *Science* 290:992-995). A double mutant, LLO S44A L461T, containing both of the preceding mutations, exhibits the properties of each of the independent mutations in one molecule, leading to activity at neutral pH and greater quantities of LLO in the host cytosol.

Each of the mutant strains displayed a growth defect in J774 macrophage-like cells over an 8-hour period (FIG. 1A). This growth defect was not due to an inability to escape from the phagosome (Table II), and was eliminated by the removal of the extracellular antibiotic gentamicin (FIG. 1B). Sensitivity to gentamicin was also observed when these strains were used to form plaques in cell culture monolayers (Table II). As seen previously (Glomski et al., supra) the bacteria with the LLO L461T allele could form plaques of equivalent size to wild-type bacteria after 3 days of growth at a low gentamicin concentration, but the plaque size decreased with increasing gentamicin. Bacteria with the LLO S44A allele could form plaques 14% the diameter of wild-type bacteria, but only at the lowest concentration of gentamicin, while the LLO S44A L461T bacteria were unable to form plaques at all.

Figure 2:
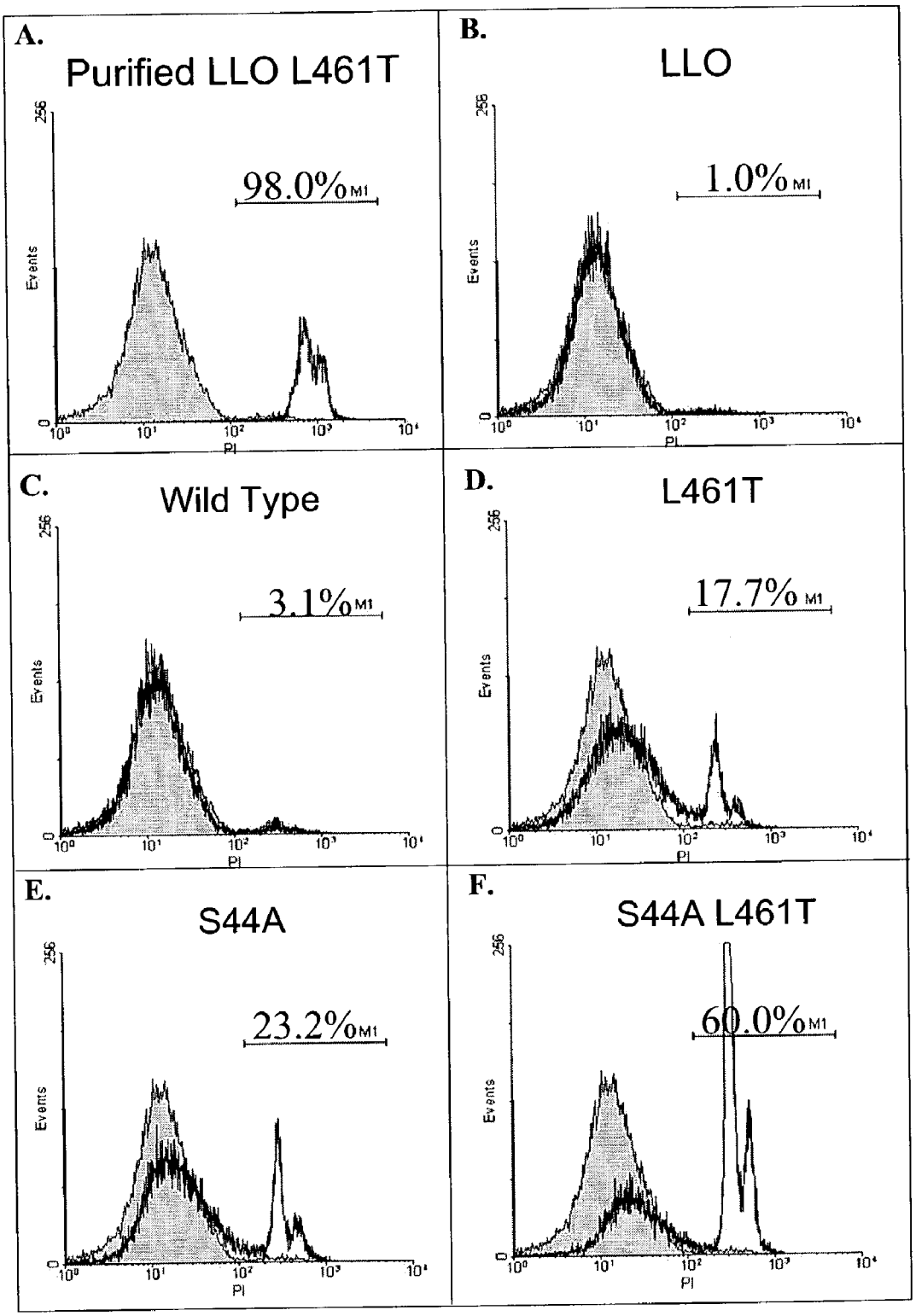
FIGS. 2A-2F. Growth of the Cytotoxic Mutants in J774 macrophage-like cells and C57BL/6 Mice. 2A) Colony forming units found within a monolayer of J774 cells on a 12 mm glass coverslip, at the indicated time, in the presence of the extracellular antibiotic gentamicin added 1 hour post-infection. Data represents the mean values derived from 3 coverslips. 2B) Colony forming units found within a monolayer of J774 cells on a 12 mm glass coverslip, at the indicated time, with gentamicin treatment from 1 hour to 2 hours post-infection. Data represents the mean values derived from 3 coverslips.

The gentamicin sensitivity of the mutant strains suggested that these strains were damaging the host cell membrane and allowing gentamicin to enter and inhibit the growth of the intracellular bacteria. Thus, plasma membrane damage was assessed by infecting bone marrow derived macrophages and monitoring host DNA staining with the membrane impermeant dye propidium iodide (FIG. 2). Using flow cytometry to quantify staining we found that 3.1% of the macrophages were permeabilized by wild-type bacteria, while 17.7%, 23.2%, and 60% were permeabilized in 4 hours by bacteria secreting LLO L461T, LLO S44A, and LLO S44A L461T, respectively. We conclude from these collective observations that these strains represent a range of bacterial cytotoxicity, starting from the least cytotoxic to the most cytotoxic, the strains can be placed in the following order: wild-type (10403S), LLO L461T, LLO S44A, and LLO S44A L461T.

2. The Greater the Cytotoxicity the Greater the Virulence Defect

Figure 3:
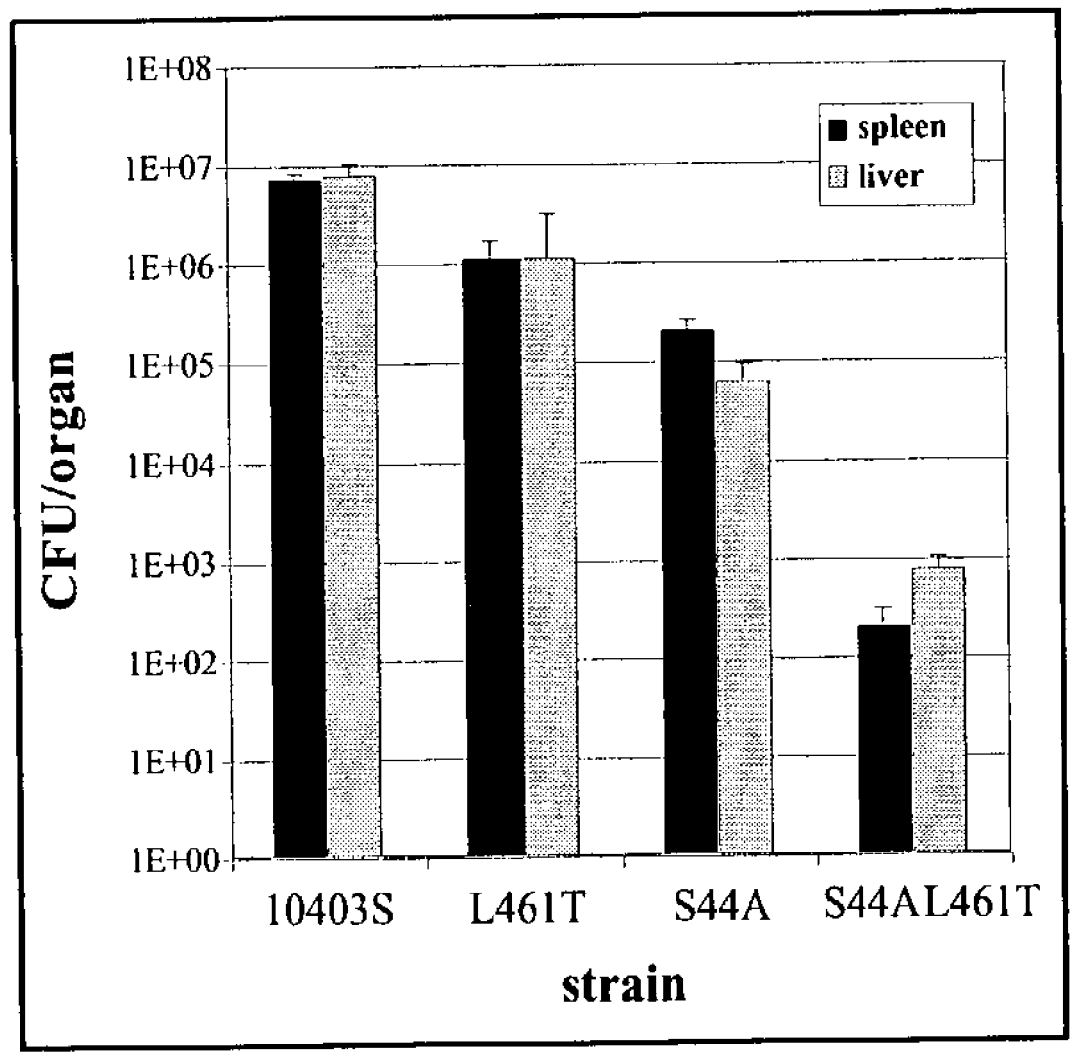
FIG. 3. The Greater the Cytotoxicity, the Less the Cytotoxic Bacteria Grow in the Mouse. $1 \times 10^5$ CFU of each strain was injected into the tail vein of C57BL/6 mice. After 24 hours the liver and spleen were removed, homogenized, and plated to determine CFU in each organ. Error bars indicate standard deviation from five mice.

We found that the more cytotoxic the strain the higher the lethal-dose 50 (Table II). Since the measurement of mouse death does not necessarily indicate the ability of bacteria to multiply inside the mouse, mice were infected for 24 hours with each strain, and colony-forming units were established for both the liver and spleen. We found that the more cytotoxic the strain, the fewer bacteria were found in both the spleen and the liver (FIG. 3). We conclude that the more cytotoxic the strain of *L. monocytogenes*, the less virulent the strain is in the mouse model of listeriosis.

A competitive index assay was performed with each mutant strain to establish a more accurate measurement of the mutants' virulence defects relative to the wild-type bacteria (Auerbuch, V., L. Lenz, and D. Portnoy. 2001. Development of a competitive index assay to evaluate the virulence of *Listeria monocytogenes* acta mutants during primary and secondary infection of mice. *Infection and Immunity*). In this assay, a one-to-one ratio of wild-type bacteria and erythromycin (erm)-resistant mutants were coinjected into mice, and the ratio of wild-type bacteria to erm-resistant (mutant) bacteria was established in the spleen and liver. We found the trend for the defect in virulence to be similar to the $LD_{50}$ (FIG. 4), where the greater the cytotoxicity of the strain the fewer bacteria were recovered, relative to the wild-type bacteria.

Figure 4:
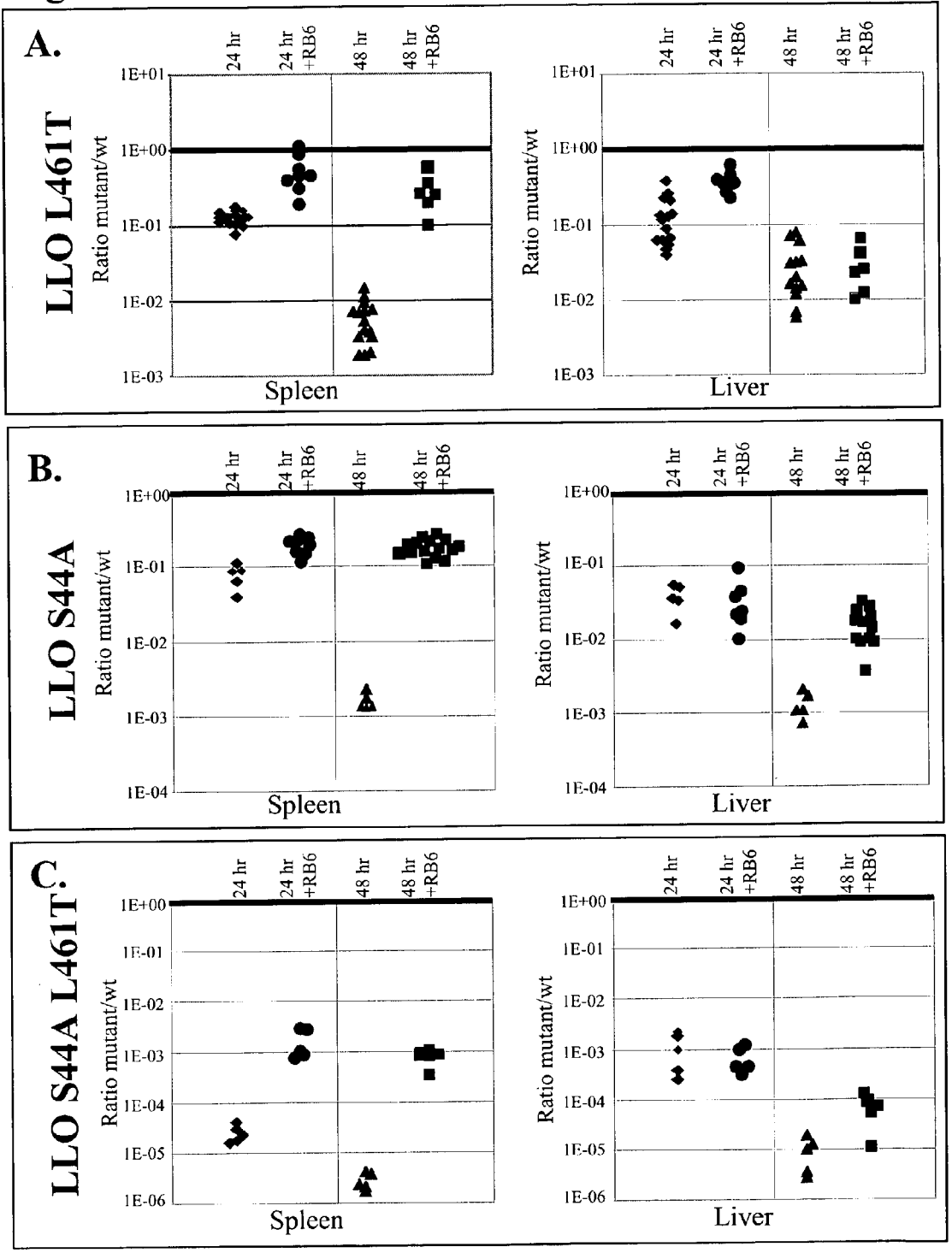
FIGS. 4A-4C. The Greater the Cytotoxicity, the Greater the Virulence Defect. A competitive index was established by injecting both wild-type bacteria and erythromycin-resistance-marked mutants into C57BL/6 mouse tail-veins. Competitive Index ratios were established in the spleen and liver by competing 4A) wild-type versus LLO L461T Erm, 4B) wild-type versus LLO S44A Erm, and 4C) wild-type versus LLO S44A L461T Erm. The y-axis indicates the ratio of the number of mutant CFU divided by the CFU of wild-type bacteria isolated from the spleen or liver of mice at the indicated time points on a log scale. Therefore, the nearer the bottom of the graph, the fewer mutant bacteria were retrieved from the mouse relative to the wild-type CFU. The ratio from each mouse is indicated with a single marker for each the spleen and liver. The "+RB6" mice were injected with the neutrophil depleting monoclonal antibody RB6-8C5 6 hours before infection with *L. monocytogenes* (Conlan and North, 1994). The bold horizontal line indicates a competitive index of 1.

3. Granulocytes are a Major Contributor to the Cytotoxic Mutants' Growth Defect in Mice A number of previous studies have shown that neutrophils contribute to early resistance to *L. monocytogenes* infection (Conlan, J. W., and R. J. North. 1994. Neutrophils are essential for early anti-*Listeria* defense in the liver, but not in the spleen or peritoneal cavity, as revealed by a granulocyte-depleting monoclonal antibody. *J Exp Med* 179:259-268; Czuprynski, C. J., J. F. Brown, N. Maroushek, R. D. Wagner, and H. Steinberg. 1994. Administration of anti-granulocyte mAb RB6-8C5 impairs the resistance of mice to *Listeria monocytogenes* infection. *J Immunol* 152:1836-1846; Gregory, S. H., A. J. Sagnimeni, and E. J. Wing. 1996. Bacteria in the bloodstream are trapped in the liver and killed by immigrating neutrophils. *J Immunol* 157:2514-2520). Indeed, neutrophils readily phagocytose and kill extracellular *L. monocytogenes* in vitro (Czuprynski, C. J., P. M. Henson, and P. A. Campbell. 1984. Killing of *Listeria monocytogenes* by inflammatory neutrophils and mononuclear phagocytes from immune and nonimmune mice. *J Leukoc Biol* 35:193-208; Rogers, H. W., M. P. Callery, B. Deck, and E. R. Unanue. 1996. *Listeria monocytogenes* induces apoptosis of infected hepatocytes. *J Immunol* 156:679-684). Therefore, since the cytotoxic strains were rapidly outcompeted by wild-type bacteria, we hypothesized that the reduced virulence observed for the cytotoxic mutants is due to sensitivity to neutrophils. To address this hypothesis we eliminated neutrophil infiltration by introducing the anti-GR1 monoclonal antibody RB6-8C5 into mice 6 hours before infection. RB6-8C5 has been shown to eliminate neutrophils from the circulation and prevent infiltration into foci of *L. monocytogenes* infection (Conlan, J. W., and R. J. North. 1994. Neutrophils are essential for early anti-*Listeria* defense in the liver, but not in the spleen or peritoneal cavity, as revealed by a granulocyte-depleting monoclonal antibody. *J Exp Med* 179:259-268). In neutropenic mice the relative virulence defect of the cytotoxic mutants was eliminated 99% in the spleen, allowing the cytotoxic mutants to grow much more similarly to the coinjected wild-type bacteria in the competitive index assay (FIG. 4). Less of an effect was observed in the liver, relative to the spleen, yet by 48 hours the more cytotoxic mutants' (LLO S44A and LLO S44A L461T) relative virulence increased 10-fold with the elimination of neutrophils. These data suggest that the cytotoxic mutants are more susceptible to neutrophil killing in immunocompetent mice.

4. A Larger Percentage of Cytotoxic Bacteria is Extracellular

Figure 5:
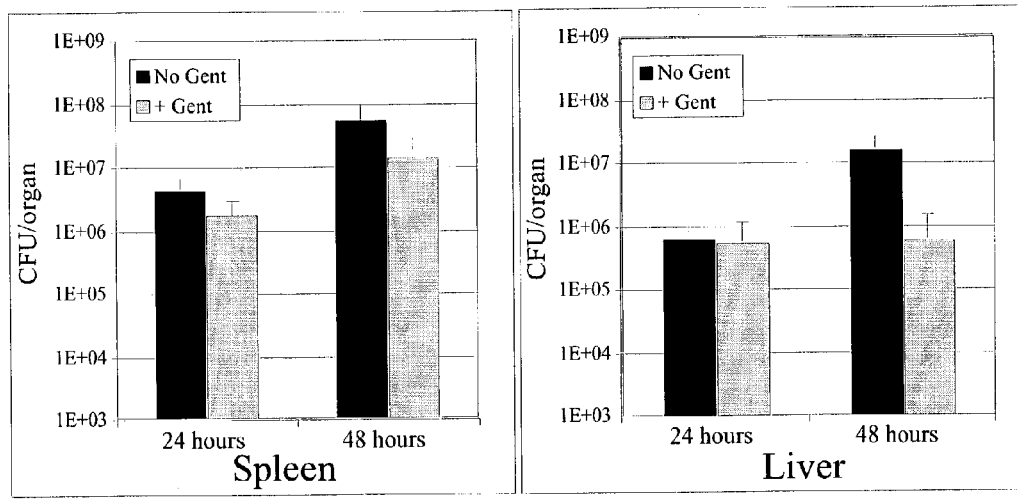
FIGS. 5A & 5B. Cytotoxic mutants are more sensitive to Gentamicin. 5A) $1 \times 10^5$ CFU wild-type bacteria were injected into the tail vein of C57BL/6 mice. 1 mg of gentamicin was injected subcutaneously, and at the indicated time the liver and spleen were removed, homogenized, and plated to determine CFU in each organ. Error bars indicate standard deviation from a minimum of 7 mice. 5B) Competitive indexes were established at 48 hours as described in FIG. 4. Data points labeled as "+RB6 gent" were injected with RB6-8C5 monoclonal antibodies 6 hours pre-infection as well as 1 mg gentamicin sulfate subcutaneously 6 hours before organ harvesting. SALT indicates data from the LLO S44A L461T strain.
Figure 5:
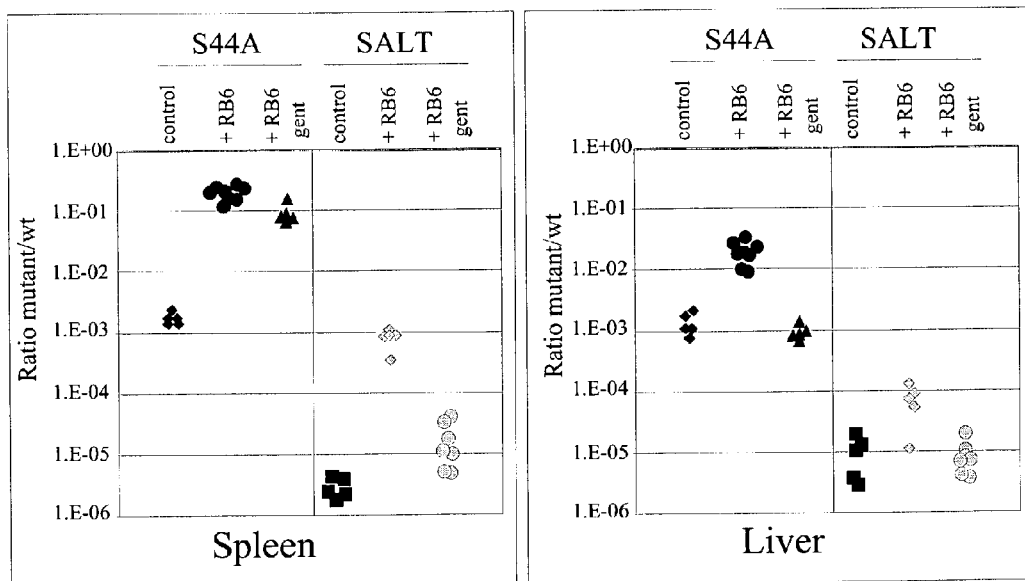

The data described in the preceding section suggested that cytotoxic strains were exposed to the extracellular environment, where neutrophils could readily phagocytose and destroy the bacteria. To further explore this possibility, we injected the antibiotic gentamicin into infected mice. Gentamicin kills extracellular bacteria without affecting intracellular bacteria (Drevets, D. A., T. A. Jelinek, and N. E. Freitag. 2001. *Listeria monocytogenes*-infected phagocytes can initiate central nervous system infection in mice. *Infect Immun* 69:1344-1350), has no significant affect on wild-type bacteria at 24 hours post-infection, and decreases the number of wild-type bacteria in the liver ten-fold at 48 hours (FIG. 5A). The sensitivity of the cytotoxic mutants to gentamicin was examined in neutropenic mice because neutrophils would likely phagocytose and destroy many extracellular bacteria, thereby obscuring our ability to detect the effects of gentamicin on extracellular bacteria. The treatment of mice with gentamicin in a competitive index assay decreased the ratio of the LLO S44A and the LLO S44A L461T mutants relative to the wild-type bacteria in the competitive index assay (FIG. 5B). By 48 hours about 99% of the LLO S44A L461T bacteria in the spleen and liver were sensitive to gentamicin, whereas LLO S44A mutants in the spleen and the LLO L461T mutants in both organs were less affected by gentamicin. However, the addition of gentamicin did not completely reconstitute the resistance of the mice to the level seen in mice containing active neutrophils.

Figure 6:
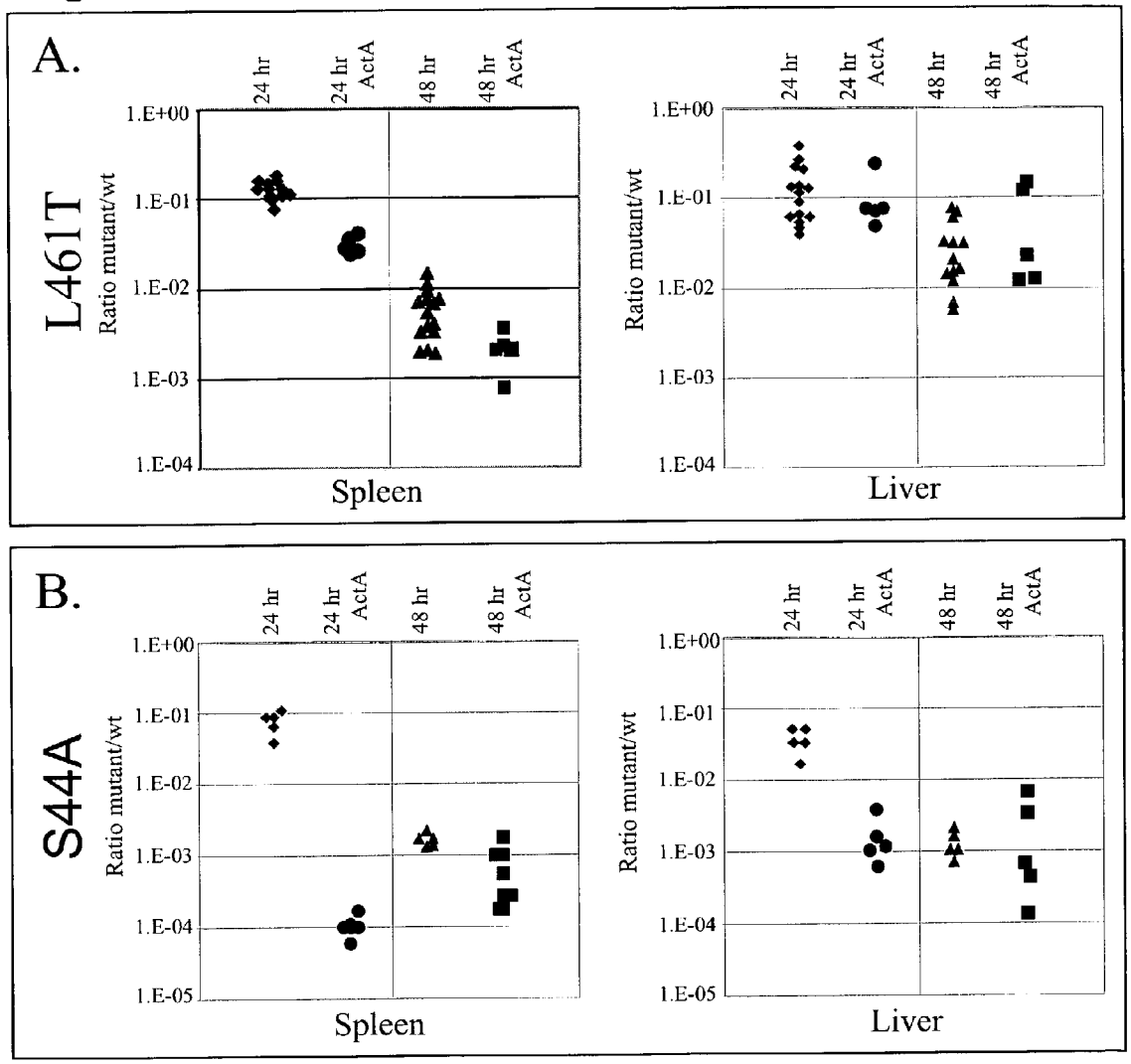
FIGS. 6A & 6B. The Virulence Defect is not Due to Defects in Cell-to-Cell Spread. Competitive indexes were performed as described in FIG. 4. For data sets indicated by "ΔActA", all strains including the reference strain, secreting wild-type LLO, contained an in-frame deletion in actA that eliminated actin-based motility. 6A) "24 hr" and "48 hr" indicate the time of organ harvest. The data points represent the ratio of erythromycin-resistant LLO L461T bacteria divided by the CFU of wild-type bacteria in the spleen and liver. "24 hr ΔActA" and "48 hr ΔActA" indicate the time of organ harvest and the ratio of erythromycin resistant ΔActA LLO L461T bacteria divided by wild-type LLO secreting bacteria without the ActA gene, recovered from the spleen and liver. 6B) Competitive index ratios established similar to A), but using LLO S44A erythromycin resistant mutants.

5. The Virulence Defect of Cytotoxic Mutants is Not Due to Defects in Cell Spread The defect observed in bacterial plaquing, in L2 monolayers, raised the concern that the cytotoxic bacteria may be damaging their host cells to such a degree that the cytoskeletal dynamics may have been disrupted. The ability of bacteria to manipulate the host cytoskeleton is vital to virulence, since bacteria that are unable to form actin tails are 10,000-fold less virulent (Brundage, R. A., G. A. Smith, A. Camilli, J. A. Theriot, and D. A. Portnoy. 1993. Expression and phosphorylation of the *Listeria monocytogenes* ActA protein in mammalian cells. *Proc Natl Acad Sci USA* 90:11890-11894). Therefore, it is conceivable that the cytotoxic mutants are less virulent because they spread less efficiently from cell to cell. To address this question, we made an in-frame deletion in the actA (ΔActA) of each of the cytotoxic mutants to eliminate the influence of cell-to-cell spread, and then performed the competitive index assay versus wild-type LLO ΔActA. If cell spread was the major factor contributing to the virulence defect of the cytotoxic mutants, then we would predict that its elimination would render the mutants similarly virulent to the ΔActA bacteria secreting wild-type LLO, nearing a ratio of 1. This was not the case. Rather, eliminating ActA function had little affect or increased the defect observed for the cytotoxic mutants (FIG. 6). Both ΔActA cytotoxic strains, secreting LLO L461T and LLO S44A, competed less well against the ΔActA with wild type LLO. The LLO S44A L461T ΔActA strain became so attenuated that there were insufficient numbers of bacteria in the liver or spleen to establish reliable colony forming units.

6. Growth of *L. monocytogenes* in Mouse Serum

Despite the fact that phagocytes are responsible for much of the growth defect of the cytotoxic bacteria in the mouse, their removal does not make the mutants grow as well as the wild-type bacteria under any of our experimental conditions. We therefore reasoned that cytotoxic bacteria might not divide at the rate afforded by the intracellular environment. Thus, we determined the doubling times of bacteria growing in mouse serum. We found that *L. monocytogenes* grows in mouse serum-native, heat deactivated, or derived from infected mice—but with a maximum doubling time of 58 minutes. This growth rate is significantly slower than the previously published maximal intracellular doubling time of 42 minutes (Glomski et al., supra). Considering that bacterial growth is exponential, a 16-minute difference in doubling time between the two different environments can quickly lead to great differences in bacterial numbers, and could thus account for some of the growth defects we observe for the cytotoxic mutants. Interestingly, bacteria grew well in fetal bovine serum and mouse serum supplemented with BHI, with doubling times of 34 minutes and 31 minutes, respectively, suggesting that mouse serum did not have an inhibitory effect, but was more likely to be nutrient limiting.

C. Discussion

In this study we presented evidence that the intracytoplasmic bacterial pathogen *L. monocytogenes* is less virulent when it compromises its intracellular niche. We used cytotoxic mutants with various levels of cytotoxicity to show that: 1) cytotoxic mutants were more sensitive to neutrophils, and 2) cytotoxic mutants were more susceptible to the extracellular antibiotic gentamicin. These data indicate that cytotoxic *L. monocytogenes* mutants are exposed to the extracellular environment and are susceptible to elimination by neutrophils. These conclusions indicate the following model to explain why *L. monocytogenes* (and possibly other intracellular pathogens) needs to balance the activity of its cytolysin, LLO, between functionality and cytotoxicity. When the cytolysin is inactive, or absent, the bacteria are phagocytosed, and are trapped and later killed in the phagosome, and thus cannot multiply. At the other extreme, an overly active LLO, due to greater biochemical activity and/or greater cytosolic quantity, are phagocytosed, escape from the phagosome, and begin to grow in the cytosol. However, these cytotoxic bacteria damage their host cell, which then exposes them to the influence of extracellular defenses and nutrient limitation that limits or terminates the infection. The wild-type bacteria fall in between these two extremes, striking a balance, controlling LLO activity to mediate the efficient lysis of the phagosome, while limiting the function of LLO to avoid damage to the host cell. This balance allows the wild-type bacteria to escape to the cytosol, multiply, and spread from cell to cell. The wild-type bacteria eventually cause enough damage to their host cell to expose them to the same environment that adversely affects the cytotoxic mutants, but it occurs at a time late enough to have allowed a larger number of bacteria to grow and to spread out of the initial cell into new host cells. As such, the wild-type bacteria can continue to spread the infection through host tissues and continue to increase bacterial numbers.

Implicit in the above model is the importance of bacterial cell-to-cell spread, thus we explored the possibility that the cytotoxic mutants' virulence defect was caused by cytotoxic disruption of the actin based cell-spread process by eliminating cell-to-cell spread via the deletion of ActA. If spreading from cell to cell was the primary mechanism by which the cytotoxic mutants were causing their growth defect, one would predict that when actin based cell-to-cell spread was eliminated the cytotoxic bacteria would grow more similarly to the ΔActA bacteria secreting wild-type LLO. This was not the case. The growth of the bacteria was unaffected or further decreased when ActA was deleted. Indeed, we observed a striking 3-log decrease in growth of the LLO S44A mutant at 24 hours, relative to a ΔActA wild-type LLO strain. As seen in previous tissue culture assays, bacteria that cannot nucleate actin are more cytotoxic, and thus the cytotoxicity of the mutants may be exacerbated by the elimination of cell spread. The simplest explanation for this observation is that the elimination of the migration of a portion of the bacteria from the initially infected cell into a new cell effectively increases the number of bacteria within the initial cell. However, the increased cytotoxicity of ActA-deleted bacteria may be more complicated than this simple hypothesis and may instead suggest a link between ActA and LLO function.

As reported previously, neutrophils were vital to limiting bacterial growth. However, they were more effective at controlling the cytotoxic mutants than wild-type bacteria, since their elimination allowed the cytotoxic bacteria to grow at a rate more similar to wild-type bacteria. We found that the cytotoxic mutants were less sensitive to the function of neutrophils in the liver than in the spleen. Based on our model, where cytotoxic mutants are exposed to extracellular defenses, there are a number of explanations that may account for these differences observed in different tissues. One possibility is that hepatocytes are capable of coping with cytotoxic bacteria better than splenic cells. If hepatocytes repair damaged membranes or resist lysis, the cytotoxic mutants would persist in a protected environment longer than in cells that were more sensitive to the lytic activity of LLO. Indeed, the ability of the liver to rapidly repair from toxic insults and tissue damage is well documented. A second possibility is that after bacteria lyse their initial host cell within the liver they can be phagocytosed by neighboring cells more readily in the liver, thus reducing their extracellular residence time. Rapid phagocytosis in the liver may be aided by the function of the bacterial protein InlB, which mediates the uptake of *L. monocytogenes* into hepatocytes, but does not mediate uptake into a number of other cell types. Eliminating InlB expression would help to determine if InlB-mediated hepatocyte phagocytosis allows cytotoxic mutants to reduce their attenuation in the liver.

We did not directly address the mechanism by which neutrophils preferentially eliminate cytotoxic mutants, but there are a number of defense strategies that could be functioning. It has been shown in previous studies that neutrophils are capable of killing *L. monocytogenes* in vitro, yet are incapable of killing intracellular bacteria within hepatocytes in tissue culture. Therefore it is likely that neutrophils simply have greater access to the cytotoxic mutants because the bacteria are extracellular. However, the importance of neutrophils in controlling wild-type infection also implies that wild-type bacteria will eventually have some degree of extracellular exposure as well. It is also possible that neutrophils selectively lyse cells infected with cytotoxic bacteria. Previous publications reported that neutrophils are capable of lysing *L. monocytogenes*-infected hepatocytes, though the mechanism, whether direct or indirect, has not been established. One might hypothesize that the lysis-targeting signal received by neutrophils from infected cells may be elicited by cell damage. Since the cytotoxic bacteria damage the host cell, the cells infected by cytotoxic bacteria would thus be targeted for lysis earlier than the wild-type bacteria.

Permeabilization of the host cell's plasma membrane may allow the efflux of activated complement or bacterial components, such as formylated peptides, that are chemoattractants of neutrophils that have been shown to be important in the mouse's resistance to *L. monocytogenes*. In this scenario, the cytotoxic bacteria would be targeted for phagocytosis and destruction earlier than the wild-type bacteria, since they would emit chemotactic signals from within damaged cells. Exposure to the lytic functions of complement is unlikely to directly affect *L. monocytogenes* since we have described, in this study, that the bacteria grow at similar rates in normal of heat-deactivated mouse serum. However, the opsonizing properties of complement may act to target the cytotoxic bacteria for more efficient phagocytosis.

An alternate explanation for the virulence defect of the cytotoxic mutants is that they are a more visible threat than the wild-type bacteria. By damaging their host cells the bacteria may cause the liberation of more inflammatory cytokines, and thereby recruit more inflammatory cells to the foci of infection, as well as activate the function of those infiltrates. A number of inflammatory cytokines, including TNFα, IFNγ, IL-1α/β and IL-6, are vital for resistance to *L. monocytogenes*. Thus, The greater presence of inflammatory cells, such as neutrophils, that are activated to a greater degree would then foster the greater clearance of the bacteria from the foci of infection.

The antibiotic gentamicin has been used in both tissue culture and in vivo as a means to eliminate extracellular bacteria. In this study we found that our two most cytotoxic mutants, secreting LLO S44A or LLO S44A L461T, were particularly sensitive to gentamicin injected into infected mice. However, this effect was only detectable when neutrophils were first eliminated. This finding indicates that the same population of bacteria that are sensitive to gentamicin are also sensitive to the activity of neutrophils. Interestingly, gentamicin did not entirely restore neutropenic mice to the level of resistance observed in immunocompetent mice. This finding indicates, in agreement with the rest of our data, that the virulence defect observed for the cytotoxic mutants is multifactoral. Additionally, the lack of gentamicin's ability to completely replace the activity of neutrophils may indicate that neutrophils are playing a broader role in bacterial clearance than simply phagocytosing and destroying extracellular bacteria.

*L. monocytogenes* is naturally auxotrophic for several amino acid and vitamins. Therefore, it is not surprising that these bacteria do not replicate as well in mouse serum as in mammalian cytoplasm. The importance of a hexose phosphate transporter (hpt) for intracytoplasmic growth of *L. monocytogenes* has previously been reported. HPT allows the bacteria to utilize glucose-1-phosphate, which is a breakdown product of glycogen in the liver. Thus, there is evidence that pathogens have not only evolved virulence factors to customize their pathogenic niche, but they may have also tuned their metabolism to each of their respective niches.

This study presents data that suggests that maintenance of the cytoplasmic niche is vital to *L. monocytogenes* pathogenesis. If these bacteria do not properly manage the lytic effects of the pore-forming cytolysin LLO, they compromise their ability to grow in the host due to pressures from the extracellular defenses. Similarly, if the host acts cytolytically on infected cells, bacterial clearance is also achieved. Indeed, cytotoxic T-lymphocytes are the primary effector cell of the adaptive immune response to *L. monocytogenes* that function to target and lyse infected cells. Thus, whether it is caused by the bacteria or by the host, the movement of *L. monocytogenes* from an intracellular compartment to an extracellular compartment reduces the ability of the bacteria to grow. To reduce its extracellular residence time *L. monocytogenes* has developed a number of virulence factors to ensure that it becomes, thrives, and remains primarily intracellular.

D. Conclusions

In this study, a series of strains with mutations in LLO were constructed with varying degrees of cytotoxicity. We found that the more cytotoxic the strain in cell culture, the less virulent they were in mice. Induction of neutropenia increased the virulence of the cytotoxic strains 100-fold in the spleen and 1 0-fold in the liver. The virulence defect was partially restored in neutropenic mice by adding gentamicin, an antibiotic that kills extracellular bacteria. Additionally, *L. monocytogenes* grew more slowly in extracellular fluid, mouse serum, than within tissue culture cells. We conclude that *L. monocytogenes* controls the cytolytic activity of LLO to maintain its intracellular nutritionally rich niche and avoid extracellular defenses of the host.

VI. IpIA Mutants: DP-L2214 and DP-L4364

To identify genes important for intracellular growth, we performed a modified intracellular methicillin selection on a transposon insertion library of *L. monocytogenes* (A. Camilli, C. R. Paynton, D. A. Portnoy, *Proc Natl Acad Sci USA* 86, 5522-6 (Jul. 1989)). A pool of Tn917-LTV3 insertion mutants was used to infect the J774 mouse macrophage cell line. At 4 hours post infection (h.p.i.), sufficient time to permit escape of bacteria from the phagosome, the infected macrophages were treated with 1 mg/ml methicillin to select against dividing bacteria. At 24 h.p.i. bacteria were harvested from the macrophage monolayer by host cell lysis and cultured in rich bacteriological media. The selection was repeated twice before isolating individual bacterial colonies. We identified three classes of mutants from the methicillin selection. The first class of mutants was phenotypically non-hemolytic on blood agar. Non-hemolytic strains of *L. monocytogenes* remain in the vacuole where they are unable to replicate and thus would not be susceptible to methicillin killing. The second class of mutants isolated consisted of threonine and pro-line auxotrophs. A third class of mutants was hemolytic and prototrophic, and therefore likely contained transposon insertions in genes important specifically for intracellular growth; one of these mutants, DP-L2214, was selected for further analysis.

DP-L2214 exhibited normal growth in both rich and minimal bacteriological media (data not shown). In contrast, replication of DP-L2214 in J774 macrophages aborted at approximately 5 h.p.i. Thus, DP-L2214 has a replication defect that is restricted to the intracellular environment. By sequencing the DNA adjacent to the transposon, we identified an open reading frame disrupted by the Tn917-LTV3 insertion. A BLAST search of the *L. monocytogenes* genome using this sequence revealed homology to the lipoate protein ligase gene (IpIA) of *Escherichia coli*, therefore we have termed this gene IpIA1 (*L. monocytogenes* EGD-e Imo0931) (SEQ ID NO 44)(Glaser et al., *Science* 294, 849-52 (Oct. 26, 2001)). The *L. monocytogenes* IpIA1 protein and DNA sequence are available on the *Listeria* genome website, Listilist, which has a website having "genolist.pasteur.fr/ListiList/" after "http://".

The published *L. monocytogenes* genome sequence also revealed the existence of a second IpIA-like gene, IpIA2 (*L. monocytogenes* EGD-e Imo0764)(Glaser et al., supra). To verify that the intracellular replication defect of DP-L2214 was due to interruption of the IpIA1 open reading frame, we constructed an in frame deletion of the IpIA1 gene and were able to complement DP-L2214 with a plasmid containing IpIA1. The ΔIpIA1 strain (DP-L4364) was characterized in an intracellular replication assay in the J774 macrophage cell line. Growth of the IpIA1 deletion strain appeared similar to DP-L2214, in doubling time and kinetics. ΔIpIA1 was also compared to DP-L2214 in a L2 fibroblast plaquing assay that measures intracellular growth over a 3 day infection. Both ΔIpIA1 and DP-L2214 exhibited plaque size that was 56% and 58% of the wildtype plaque size respectively. In addition, we observed a unique mixed plaquing phenotype associated with both ΔIpIA1 and DP-L2214; the standard deviation from the average plaque size was 3 times greater in the mutants than in the wildtype strain. Surprisingly, plaque size and frequency of the ΔIpIA1 mutant and DP-L2214, but not the wildtype strain, were negatively affected by a decrease in thickness of the agar overlay. Taken together, these results strongly suggest that disruption of the IpIA1 ORF by Tn917 in DP-L2214 resulted in a loss of function and is responsible for the intracellular replication defect.

*E. coli* IpIA ligates free lipoic acid to the E2 subunit of pyruvate dehydrogenase (PDH) and other structurally related enzymes(D. E. Brookfield, J. Green, S. T. Ali, R. S. Machado, J. R. Guest, *FEBS Lett* 295, 13-6 (Dec. 16, 1991). Using an antibody that recognizes lipoic acid, we analyzed the profile of lipoylated proteins in *L. monocytogenes* grown in broth culture by Western blot. In brain-heart infusion (BHI) broth, a rich bacteriological media, the anti-LA antibody revealed one dominant protein that was identified as the *L. monocytogenes* E2 subunit of pyruvate dehydrogenase by mass spectroscopy. No difference in lipoylation of E2 PDH was observed between the wildtype and the ΔIpIA1strain. These data identify E2 PDH as a major target of lipoic acid modification in *L. monocytogenes*, consistent with reported observations in *E. coli*. We next determined the lipoylation state of E2 PDH in *L. monocytogenes* during intracellular growth. J774 macrophages were infected with either wildtype *L. monocytogenes* or the ΔIpIA1mutant strain at high multiplicity of infection (m.o.i.) such that the majority of cells contained 1 or more bacteria. At 4 h.p.i. total cell lysates were prepared from intracellular bacteria for SDS-PAGE and Western blot analysis. Equivalent loading of bacterial proteins was confirmed by Western Blot analysis of an unrelated protein, ActA. While lipoylated E2 PDH was observed in wildtype bacteria grown in macrophages, the modified form of E2 PDH was not present in ΔIpIA1 lysates.

The pool of modified E2 PDH present in the bacterial innoculum after overnight culture in rich media may have allowed the ΔIpIA1 strain to undergo approximately 4 rounds of cell division in the host cell over 5 hrs before depleting functional E2 PDH. If lipoylated E2 was depleted after several rounds of cells division, ΔIpIA1 mutant bacteria isolated from host cells should not be able to establish a productive infection. We isolated wildtype and mutant bacteria from infected macrophages 4 h.p.i. and used these bacteria to infect a new monolayer of macrophages. During the subsequent infection the wildtype strain grew very aggressively while the ΔIpIA1 strain did not replicate at all. Thus, despite the presence of a second lipoate protein ligase in the genome, we conclude that IpIA1 performs a critical and non-redundant function during intracellular growth that involves modification of E2 pyruvate dehydrogenase.

Lipoic acid has been shown to have anti-oxidant properties in mammalian cells (L. Packer, *Drug Metab Rev* 30, 245-75 (May, 1998)). Therefore, we considered the possibility that lipoic acid in *L. monocytogenes* as part of the PDH complex might also act to protect the bacteria from oxidative stress in the host cell. Host cells may have several sources of oxidative stress. First, macrophages are able to produce reactive oxygen and nitrogen intermediates in response to phagocytosis. Secondly, all cells produce reactive oxygen species as a normal by-product of oxidative metabolism. We observed that in an L2 plaquing assay, a change in the thickness of the agar overlay, which would increase oxygen permeability to the fibroblast monolayer, caused a 25% decrease in average plaque size and number of plaques formed by the ΔIpIA1strain compared to wildtype. To further investigate the role of IpIA1 in protection from oxidative stress, we tested intracellular bacteria for DNA damage using the TUNEL assay to detect free 3'OH ends. Reactive oxygen species cause oxidation of nucleic acids, as well as proteins and lipids; therefore, we reasoned that bacteria in an environment of oxidative stress should exhibit DNA strand breaks. Primary bone marrow derived macrophages were infected with either wildtype *L. monocytogenes* or ΔIpIA1. At 9 h.p.i., the macrophages were subjected to TUNEL staining. We were able to observe TUNEL positive bacteria in macrophages infected by the ΔIpIA1mutant strain, but not macrophages infected by wildtype bacteria. Although the incidence of TUNEL positive bacteria was rare, they occurred in clusters, such that the TUNEL positive bacteria in one cluster were contained within one host cell. The presence of DNA strand breaks in ΔIpIA1mutant bacteria supports the hypothesis that E2-lipoamide protects bacteria against oxidative stress.

Our cell culture assays revealed a role for IpIA1 in intracellular replication in macrophages. We also tested the virulence of the ΔIpIA1mutant in an intravenous (i.v.) mouse model of infection by determining the $LD_{50}$. (See Auerbach et al., supra). In the Balb/c background, the $LD_{50}$ of the IpIA1mutant strains were 250 to 300-fold less virulent than the wildtype parental *L. monocytogenes* strain (Table 4).

TABLE IV

| Strain | Genotype | Phenotype | $LD_{50}$ |
|---|---|---|---|
| 1040S | Wildtype | Wildtype | $2 \times 10^4$ |
| DP-L2214 | lpIA1::Tn917 | Abortive Growth | $6 \times 10^6$ |
| DP-L4364 | ΔIpIA1 | Abortive Growth | $5 \times 10^6$ |

Although the IpIA1 mutants were less virulent, they stimulated a robust $CD8^+$ T cell response suggesting that these strains may be promising candidates for vaccine development (data not shown). Our in vivo experiments highlight the important role of IpIA1 in *L. monocytogenes* pathogenesis and suggest that utilization of lipoic acid is important for growth of bacterial pathogens in the host.

All organisms have mechanisms to increase survival and replication in response to stress. As an intracellular pathogen, *L. monocytogenes* must be able replicate in cytosolic conditions. Although it is difficult to define comprehensively what components of the cytosol are required for bacterial growth and survival, the methicillin selection allowed us to functionally identify genes important for growth in the cytosol. The selection of the IpIA1::Tn917 mutant by methicillin, despite the presence of a second lipoate protein ligase, IpIA2, suggests that *L. monocytogenes* encounters lipoic acid in a restricted form in the host cytosol that requires an additional lipoate protein ligase activity for intracellular growth. *E. coli* also has two lipoate protein ligases, IpIA and LipB, that transfer lipoic acid from different sources to E2 PDH (T. W. Morris, K. E. Reed, J. E. Cronan, Jr., *J Bacteriol* 177, 1-10 (Jan., 1995); K. E. Reed, J. E. Cronan, Jr., *J Bacteriol* 175, 1325-36 (Mar., 1993)). *E. coli* LipB utilizes de novo synthesized lipoic acid from octanoyl-acyl carrier protein. *E. coli* IpIA ligates scavenged free lipoic acid to E2 PDH. *L. monocytogenes* is a lipoic acid auxotroph, and uses lipoic acid scavenged from its environment; maintenance of two lipoate protein ligase genes in the genome implies different external sources of lipoic acid. Studies of lipoic acid metabolism in mammalian cells suggest that very little free lipoic acid is present in the cytosol under normal physiological conditions. Thus, we hypothesize that in *L. monocytogenes*, IpIA2 may play a role in nutrient rich conditions when free lipoic acid is available, but IpIA1 is more important in the host cell where lipoyl groups may have to be scavenged from peptides transported from the cytosol. *L. monocytogenes* is known to use peptides from the host cytosol as a source for amino acids. As E2 PDH is an abundant protein in all organisms, it is likely that peptides modified by lipoamide would be available in the host cytosol due to normal protein turnover. The enzymatic specificities of IpIA1 and IpIA2 are unknown and will be the subject of future investigation.

Our data show that E2 PDH is the primary target of IpIA1 in *L. monocytogenes*. Previous research has focused on the function of PDH in intermediary metabolism in converting pyruvate into acetyl CoA which represents the entry of carbon into the tricarboxylic acid cycle. The metabolic function of PDH, which requires the E1, E2 and E3 subunits, is important for aerobic growth, and lack of PDH enzymatic activity is likely responsible for the abortive growth phenotype we have observed in the ΔIpIA1 mutant strain. However recent studies have revealed novel functions for the E2 subunit of PDH that appear independent of the PDH holoenzyme. E2 and E3, required for the redox capacity of lipoamide, contribute to the reducing capacity of a protein complex isolated from *Mycobacterium tuberculosis* extracts. This reducing activity may mediate *M. tuberculosis* resistance to oxidative stress in vivo. Our data showing that the IpIA1 strain is more susceptible to oxidative stress are consistent with this hypothesis. In addition, studies in *Pseudomonas aeruginosa, B. subtilis*, and *B. thuringensis* have revealed a role for E2 PDH in DNA binding and/or transcriptional regulation. The requirement for lipoamide modification in those processes is not known. The abortive growth phenotype we observe in IpIA1 mutants is due primarily to a defect in PDH metabolic function. However, the possibility that E2-lipoamide may also regulate other bacterial processes during an *L. monocytogenes* infection, such as protection from oxidative stress or transcriptional regulation, remains to be explored. Like *L. monocytogenes*, some other bacterial species, including *Chlamydia trachomatis, Staphylococcus aureus* and *Streptococcus pyogenes*, also have two IpIA-like genes but no lipB homolog, suggesting that utilization of host derived lipoic acid may be critical for replication of many bacterial pathogens.

VII. Use of DP-L4017 as a Vaccine

One hundred and twenty Balb/c mice are divided into three groups of 40. One group is immunized with one-tenth of an $LD_{50}$ of wild-type *L. monocytogenes*, one group is immunized with sterile saline and the third group is immunized with a recombinant *L. monocytogenes* vaccine vector which is based on the attenuated DP-L4017 strain that is transformed to secrete influenza nucleoprotein (LM-NP). After two weeks, each group receives a similar booster immunization. This immunization schedule is determined to produce strong CTL responses against influenza nucleoprotein. Two weeks after the last immunization, animals in each group are challenged subcutaneously with either CT26 or RENCA tumor cell lines which have been transfected with the same influenza nucleoprotein gene that was used to transform the *L. monocytogenes* vector (CT26-NP or RENCA-NP, respectively) or with the parental CT26 or RENCA line. Each mouse is administered $5 \times 10^5$ tumor cells subcutaneously via the flank. Tumor growth is monitored every two days in these six groups of animals by direct measurement of the diameter of the tumor. Efficacy of the vaccine is demonstrated by observing slower growing tumors or the absence of tumors in mice vaccinated with LM-NP and administered a tumor cell line expressing NP.

CTL Generated by Immunizing Balb/c Mice with LM-NP Can Kill Tumor Cells CT26 and RENCA that Express NP In Vitro Mice are immunized with 0.1 $LD_{50}$ of LM-NP. Two weeks later, the mice are sacrificed and primary cultures are set up of spleen cells with either influenza infected (A/PR8/34) splenocytes or with a synthetic peptide 147-158 known to represent the immunodominant epitope of the NP protein. After four days in culture, the cytolytic activity of both populations is measured against CT26-NP, RENCA-NP and the parental cell lines CT26 and RENCA. A positive control is included (P815, a mastocytoma tumor cell line known to be efficiently lysed by $H-2^d$ restricted CTL in the presence of the peptide or when infected by A/PR8/34). RENCA-NP and CT26-NP, but not the parental lines, are lysed by NP specific effectors induced by immunizing with LM-NP and expanded with A/PR8/34. A similar experiment in which the effectors are expanded with peptide show similar results.

It is evident from the above results and discussion that the present invention provides important attenuated *Listeria* strains that find use in a variety of different applications. As such, the present invention represents a significant contribution to the art.

All publications and patent application cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An attenuated *Listeria* bacterium having an inactivating mutation in a lipoate protein ligase (IpIA) gene having SEQ ID NO:44 and a mutation in a lysteriolysin O (hly) gene having SEQ ID NO:43, wherein said mutation in said hly gene is not a deletion mutation that removes said hly gene's entire PEST sequence coding domain found in the N-terminal 75 residues of the LLO protein, and wherein said mutation in said hly gene is in a coding region of said hly gene and said mutated hly gene encodes an LLO protein that is at least two-fold more hemolytic at neutral pH than wild-type LLO having SEQ ID NO:43;

wherein said mutation is at a codon encoding amino acid residue 44 or 461 of a wild type *Listeria monocytogenes* LLO protein being encoded by said hly gene having SEQ ID NO:43.

2. The attenuated *Listeria* bacterium according to claim 1, wherein said mutated hly gene encodes an LLO protein that is at least five-fold more hemolytic than wild-type LLO.

3. The attenuated *Listeria* bacterium according to claim 1, wherein said mutation is at a codon encoding amino acid residue 461 of a wild type *Listeria monocytogenes* LLO protein being encoded by said hly gene having SEQ ID NO:43.

4. The attenuated *Listeria* bacterium according to claim 3, wherein said mutation results in a threonine at amino acid residue 461.

5. The attenuated *Listeria* bacterium according to claim 1, wherein said mutation is a point mutation that modifies a MAPK phosphorylation site within the amino acid sequence of said PEST sequence.

6. The attenuated *Listeria* bacterium according to claim 5, wherein said point mutation is at a codon encoding amino acid residue 44 of a wild type *Listeria monocytogenes* LLO protein being encoded by said hly gene having SEQ ID NO:43.

7. The attenuated *Listeria* bacterium according to claim 6, wherein said point mutation results in an alanine at amino acid residue 44.

8. The attenuated *Listeria* bacterium according to claim 1, wherein said mutation in said IpIA gene is a deletion mutation.

9. The attenuated *Listeria* bacterium according to claim 1, wherein said mutation in said IpIA gene is a point mutation.

10. The attenuated *Listeria* bacterium according to claim 9, wherein said bacterium is *Listeria monocytogenes.*

11. The attenuated *Listeria* bacterium according to claim 1, wherein said bacterium further comprises a heterologous nucleic acid.

12. The attenuated *Listeria* bacterium according to claim 11, wherein said heterologous nucleic acid is integrated into the *Listeria* chromosome.

13. The attenuated *Listeria* bacterium according to claim 11, wherein said heterologous nucleic acid encodes at least one product.

14. The attenuated *Listeria* bacterium according to claim 13, wherein said at least one product is an antigen.

15. The attenuated *Listeria* bacterium according to claim 1, further comprising a heterologous gene present on a vector.

16. An immunogenic composition comprising attenuated *Listeria* bacteria having an inactivating mutation in the IpIA gene having SEQ ID NO:44 and a mutation in the hly gene having SEQ ID NO:43, and wherein said mutation in said hly gene, is in a coding region of said hly gene and said mutated hly gene encodes an LLO protein that is at least two-fold more hemolytic at neutral pH than wild-type LLO having SEQ ID NO:43;
   wherein said mutation is at a codon encoding amino acid residue 44 or 461 of a wild type *Listeria monocytogenes* LLO protein being encoded by said hly gene having SEQ ID NO:43.

17. The immunogenic composition according to claim 16, wherein said point mutation is at a codon encoding amino acid residue 461 of a wild type *Listeria monocytogenes* LLO protein being encoded by said hly gene having SEQ ID NO:43.

18. The immunogenic composition according to claim 17, wherein said point mutation results in a threonine at amino acid residue 461.

19. The immunogenic composition according to claim 16, where said mutated hly gene encodes a mutant LLO protein from *Listeria* monocytogenes and comprises a mutation in said hly gene's PEST sequence coding domain.

20. The immunogenic composition according to claim 19, wherein said mutation modifies a MAPK phosphorylation site within the amino acid sequence of said PEST sequence.

21. The immunogenic composition according to claim 20, wherein said mutation is at a codon encoding amino acid residue 44 of a wild type *Listeria monocytogenes* LLO protein being encoded by said hly gene having SEQ ID NO:43.

22. The immunogenic composition according to claim 21, wherein said mutation results in an alanine at amino acid residue 44.

23. The immunogenic composition according to claim 16, wherein said mutation in said IpIA gene is a deletion mutation.

24. The immunogenic composition according to claim 16, wherein said mutation in said IpIA gene is a point mutation.

25. The immunogenic composition according to claim 16, wherein said bacteria are *Listeria monocytogenes*.

26. A method of eliciting or boosting a cellular immune response in a mammal, said method comprising:
   administering to said mammal an effective amount of an immunogenic composition according to claim 16 to elicit or boost a cellular immune response in said mammal.

27. A method of eliciting or boosting a cellular immune response in a mammal to an antigen, said method comprising:
   administering to said mammal an attenuated *Listeria* bacteria in conjunction with said antigen, or an attenuated *Listeria* bacteria that encodes a heterologous antigen, and expresses said antigen to elicit or boost a cellular immune response to said antigen in said mammal, wherein said attenuated *Listeria* bacteria has a mutation in a gene selected from the group consisting of the IpIA gene having SEQ ID NO:44 and the hly gene having SEQ ID NO:43,
   and wherein said mutation in said hly gene is in a coding region of said hly gene and said mutated hly gene encodes an LLO protein that is more hemolytic at neutral pH than wild-type LLO having SEQ ID NO:43;
   wherein said mutation is at a codon encoding amino acid residue 44 or 461 of a wild type *Listeria monocytogenes* LLO protein being encoded by said hly gene having SEQ ID NO:43.

28. A method of delivering a nucleic acid or protein into a cell, said method comprising:
   introducing into said cell an attenuated *Listeria* bacteria, wherein said attenuated *Listeria* bacteria has a mutation in a gene chosen from the IpIA gene having SEQ ID NO:44 and the hly gene having SEQ ID NO:43 and comprises nucleotide coding sequence for said nucleic acid or protein, and wherein said mutation in said hly gene is in a coding region of said hly gene and said mutated hly gene encodes an LLO protein that is more hemolytic at neutral pH than wild-type LLO having SEQ ID NO:43;
   wherein said mutation is at a codon encoding amino acid residue 44 or 461 of a wild type *Listeria monocytogenes* LLO protein being encoded by said hly gene having SEQ ID NO:43.

29. An attenuated *Listeria* bacterium having a mutation in a hly coding sequence comprising a point mutation at a codon encoding amino acid residue 461 of a wild type *Listeria monocytogenes* LLO protein being encoded by said hly gene having SEQ ID NO:43,
   wherein said mutated hly gene encodes an LLO protein that is at least two-fold more hemolytic than wild-type LLO.

30. The attenuated *Listeria* bacterium according to claim 29, wherein said point mutation results in a threonine at amino acid residue 461.

31. The attenuated *Listeria* bacterium according to claim 29, further comprising a mutant hly coding sequence present on a vector.

32. An immunogenic composition comprising the Attenuated *Listeria* bacterium of claim 29.

33. An attenuated *Listeria* bacterium comprising an inactivating mutation in a genomic gene encoding lipoate protein ligase (IpIA) having SEQ ID NO:44.

34. The attenuated *Listeria* bacteria of claim 33, wherein the mutation is one or more of a deletion mutation, a point mutation, or a mutation that interrupts the IpIA open reading frame (ORF).

35. The attenuated *Listeria* bacteria of claim 33, wherein the *Listeria* bacterium is *Listeria monocytogenes*.

36. An immunogenic composition comprising the Attenuated *Listeria* bacterium of claim 33.

* * * * *